United States Patent [19]
Jones et al.

[11] Patent Number: 5,929,266
[45] Date of Patent: Jul. 27, 1999

[54] CHIRAL ORGANOMETALLIC COMPOUNDS

[75] Inventors: Raymond Vincent Heavon Jones, Scotland, United Kingdom; Michael Charles Henry Standen, Daphne, Ala.; Richard John Whitby, Hampshire; Jane Louise Bell, Hope Valley, both of United Kingdom

[73] Assignee: Zeneca Limited, London, United Kingdom

[21] Appl. No.: 08/894,322

[22] PCT Filed: Feb. 6, 1996

[86] PCT No.: PCT/GB96/00264

§ 371 Date: Nov. 3, 1997

§ 102(e) Date: Nov. 3, 1997

[87] PCT Pub. No.: WO96/25420

PCT Pub. Date: Aug. 22, 1996

[30] Foreign Application Priority Data

Feb. 14, 1995 [GB] United Kingdom ............... 9502870

[51] Int. Cl.$^6$ .................. C07F 17/00; C07F 7/00
[52] U.S. Cl. .................. 556/53; 556/11; 556/12; 502/103; 502/117; 526/160; 526/943
[58] Field of Search .................. 556/53, 11, 12; 502/103, 117; 526/160, 943

[56] References Cited

FOREIGN PATENT DOCUMENTS 0321853  6/1989  European Pat. Off. .

OTHER PUBLICATIONS

Besancon et al., C. R. Hebd. Seances Acad. Sci., Ser. C, vol. 288, No. 3, pp. 121–123, 1979.

Erker et al: "Stereoselective propene polymerization at a metallocene/akumoxane catalyst derived from the chirally–substituted meso–like (p–R,p–S)–bis[neoisopinocamphyl]–4,5,6,7–tetrahydroindenyl]–zirconium dichloride", Journal of Organometallic Chemistry, 450 (1993) pp. 1–7.

Erker et al: "The Role of Torsional Isomers of Planarly Chiral Nonbridged Bis(idenyl)metal Type Complexes in Stereoselective Propene Polymerization", J. Am. Chem Soc, 1993, 115, pp. 4590–4601.

Cesarotti et al: "Synthesis of New Ligands for Transition Metal Complexes: Menthyl–and Cyclopentadienes", Journal of Organomietallic Chemistry, 162 (1978) pp. 297–309.

Chemical Abstracts, vol. 123, No. 11, Sep. 11, 1995, abstract No. 144170, "Crystal and molecular structure of a new mono–substituted titanocene complex, {(.eta.5–Cp)[.eta.5–(1(4Meo)C6H4)C6H10Cp](TiCl2)}.cntdot.0.3(n–C6H14)"XP002001356 see abstract & Jiegou Huaxue (Jhuadf,02545861);95;vol. 14 (2); pp. 83.7, Chinese Acad.Sci.;Changchun Inst.Applied Chem.;Changchun;130022, Peop.Rep.China.

Chemical Abstracts, vol. 120, No. 21, May 23, 1994 Columbus, Ohio, US; abstract No. 270649, Liu Y et al: Synthesis of chiral zirconocenes with chirality on the zirconium atom: XP002001357 see abstract & Youji Huaxue (YCHHDX, 02532786);93; vol. 13(5); pp. 476–481, Chin. Acad. Sci.;Shanghai Inst. Org. Chem.; Shanghai;200032; Peop. Rep. China.

Chemical Abstracts, vol. 113, No. 19, Nov. 5, 1990 Colubus, Ohio, US: abstract No. 172255, Qian Y et al: "Organotitanium chemistry. Part 17. Substituent effects on the isomerization of 1,5–hexadiene catalyzed by ring–substituted titanocene hydride"XP002001358 see abstract & J. Mol. Catal. (JMCADS,03045102);90;vol. 60 (1); pp. 19–30, Acad. Sin.;Shanghai Inst. Org. Chem.; Shanghai; 200032; Peop. Rep. China.

Chemical Abstrats, vol. 111, No. 18, Oct. 30, 1989 Columbus, Ohio, US; abstract No. 154420, Yu B et al: Olefin polymerization with zirconocene–aluminoxane homogeneous catalysts. I. Studies on aluminoxane and propylene polymerization: XP002001359 see abstract & Gaofenzi Cailiao Kexue Yu Gongcheng (GCKGEI, 10007555);88; vol. 4(6); pp. 23–31, Beijing Res. Inst. Chem. Ind.;Beijing; Peop. Rep. China.

(List continued on next page.)

Primary Examiner—Porfiro Nazario-Gonzalez
Attorney, Agent, or Firm—Pillsbury Madison & Sutro

[57] ABSTRACT

A chiral, organometallic compound which, at a molecular level, has no C2 symmetry and comprises a carbon to carbon bond joining a chiral carbon atom to a carbon atom of a cyclopentadiene ring that is non-symmetrically substituted. Examples of such compounds include compounds of formula (I):

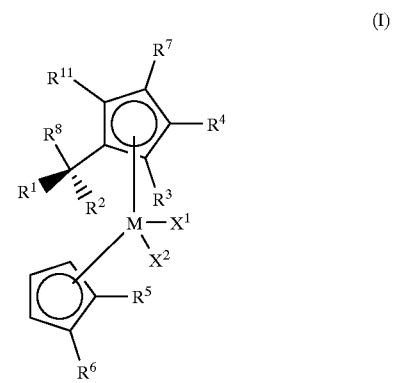

(I)

wherein $X^1$ and $X^2$ are, independently, groups which are removable during a chemical reaction; M is titanium, zirconium or hafnium; and $R^{1-8,11}$ are as specified in the description.

19 Claims, No Drawings

OTHER PUBLICATIONS

Chemical Abstracts, vol. 110, No. 11, Mar. 13, 1989 Columbus, Ohio, US; abstract No. 095442, Chen S et al: "Synthesis and addition reaction for bis(cyclohexenylcyclopentadien yl) IVB Group metal derivatives" XP002001360 see abstract & Kexue Tongbao (Foreign Lang. Ed.) (KHTPBU, 04540948);88; vol. 33 (8); pp. 648–650, Nankai Univ.;Inst. Elemental–Org. Chem.; Tianjin; Peop. Rep. China.

Chemical Abstracts, vol. 101, No.7. Aug. 13, 1984 Columbus, Ohio, US; abstract No. 055255, Chen S et al: "Synthesis and reaction of unsaturated substituted cyclopentadienylti-tanium derivatives" XP002001361 see abstract & Huaxue Xuebao (HHHPA4, 05677351);84;vol. 42(2); pp. 163–167, Nankai Univ.;Inst. Elemental–Org. Chem.; Tianjin; Peop. Rep. China.

Chemical Abstracts, vol. 096, No. 13, Mar. 29, 1982 Columbus, Ohio, US; abstract No. 103396 Cesarotti E et al: "Chiral cyclopentadienyl[s] as ligands in homogeneous asymmetric catalysis. Part 1. Asymmetric hydrogenation of simple olefins by titanium(IV) complexes" XP002001362 see abstract & J. Mol. Catal. (JMCADS,03045102);81;vol. 12 (1); pp. 63–69, Univ. Milan; Ist. Chim. Gen. Inorg.; Milan; 20133; Italy.

Chemical Reviews, No. 5, 1992, pp. 965–994, XP000537465 Halterman, R.L.: "synthesis and application of chiral cyclopentadienylmetal complexes" see the whole document.

Chemical Abstracts, vol. 124, No. 5, Jan. 29, 1996 Columbus, Ohio, US; abstract No. 056154, Paquette L A et al: "Catalytic Enantioselective Hydrogenation of 1, 1–Disub-stituted Alkenes with Optically Active Titanocene and Zir-conocene Complexes Containing either Identical or Different Ligands" XP002001363 see abstract & Organometallics (ORGND7,02767333);95;vol. 14 (10); pp. 4865–4878, Ohio State University; Evans Chemical Laboratories;Columbus;43210; OH; USA (US).

CHIRAL ORGANOMETALLIC COMPOUNDS

This application is the national phase of international application PCT/GB96/00264, filed Feb. 6, 1996 which was designated the U.S.

The present invention relates to organometallic, chiral compounds useful in asymmetric synthesis, to processes for preparing said compounds and to a method of using them in industrial processes to produce chiral products.

Various organometallic, chiral compounds are known for asymmetric synthesis (such as from DE4218199).

The present invention provides a chiral, organometallic compound which, at a molecular level, has no C2 symmetry and comprises a carbon to carbon bond joining a chiral carbon atom to a carbon atom of a cyclopentadiene ring that is non-symmetrically substituted. By having a cyclopentadienyl ring that is not symmetrically substituted the organometallic compound possesses planar chirality and by having a chiral group attached to the non-symmetrically substituted cyclopentadiene ring the faces of the cyclopentadiene are diastereotopic. Also, once complexed to the metal of the organometallic compound, the non-symmetrically substituted cyclopentadiene ring provides two control elements for enantioinduction.

In one aspect the present invention provides a compound of formula (I), wherein $X^1$ and $X^2$ are, independently, groups which are removable during a chemical reaction; M is titanium, zirconium or hafnium; and (a) $R^8$ and $R^{11}$ are hydrogen; $R^1$ and $R^2$ are different and are trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ and $R^2$ join to form an asymmetrically substituted $C_{3-8}$ cycloalkyl, $C_{3-8}$ cycloalkenyl or $C_{3-8}$ heterocyclyl ring optionally substituted with hydroxy, trialkylsilyl, alkyl, alkoxy, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^3$, $R^4$, $R^5$, $R^6$ and $R^7$ are the same or different and are selected from the substituents already recited for $R^1$; $R^4$, $R^5$, $R^6$ and $R^7$ may also be, independently, hydrogen; or, one or more of $R^3$ and $R^4$, $R^4$ and $R^7$ or $R^5$ and $R^6$ join to form an optionally substituted saturated or unsaturated ring optionally comprising one or more heteroatoms; or $R^3$, $R^4$ or $R^7$ joins with $R^5$ to form an optionally substituted $C_{1-3}$ alkyl or optionally substituted silyl bridge; or (b) $R^3$ and $R^8$ or $R^1$, $R^3$ and $R^8$ join to form an optionally substituted non-aromatic ring system optionally comprising one or more heteroatoms; or $R^1$ and $R^2$ are different and are hydrogen, trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; one of $R^4$ and $R^{11}$ must be hydrogen the other being selected from the substituents already recited for $R^2$ apart from hydrogen; $R^5$, $R^6$ and $R^7$ are the same or different and are selected from the substituents already recited for $R^2$; or, one or more of $R^4$ or $R^{11}$ (whichever is not hydrogen) and $R^7$ or $R^5$ and $R^6$ join to form an optionally substituted saturated or unsaturated ring optionally comprising one or more heteroatoms; or $R^3$, $R^7$ or $R^4$ or $R^{11}$ (whichever is not hydrogen) joins with $R^5$ to form an optionally substituted $C_{1-3}$ alkyl bridge or optionally substituted silyl bridge.

Alkyl groups and the alkyl part of alkoxy groups have straight or branched chains. They preferably contain from 1 to 10, especially 1 to 6 (for example 1 to 4) carbon atoms, and are, for example, methyl, ethyl, iso-propyl, tert-butyl or n-hexyl. Alkyl and alkoxy groups are optionally substituted, especially optionally substituted by trialkylsilyl or alkoxy.

Aryl includes naphthyl but is preferably phenyl.

Trialkylsilyl groups are especially $C_{1-8}$ alkyl$_3$Si, for example $(CH_3)_3Si$.

Cycloalkyl and cycloalkenyl rings preferably contain from 3 to 8, especially from 3 to 6, carbon atoms. They are, for example, cyclopropyl, cyclopentyl, cyclohexyl or cyclohexenyl. Cycloalkyl and cycloalkenyl rings are optionally substituted by hydroxy, alkoxy, alkyl, aryl or arylalkyl groups.

Arylalkyl is preferably phenyl($C_{1-4}$)alkyl and is, for example, benzyl, 1-phenyleth-1-yl, 2-phenyleth-1-yl, 2-phenylprop-2-yl, 1-phenylprop-2-yl or 1-phenyl-2-methylprop-2-yl.

Aryloxyalkyl is preferably phenoxy($C_{1-4}$)alkyl and is, for example, phenoxymethyl or 1- or 2-phenoxyethyl.

Alkoxyalkyl and alkoxyalkoxyalkyl are preferably $C_{1-6}$ alkoxy($C_{1-6}$)alkyl and $C_{1-6}$ alkoxy($C_{1-6}$)alkoxy($C_{1-6}$)alkyl respectively. They are, for example, methoxymethyl, ethoxymethyl or methoxy(ethoxymethyl).

Cycloalkylalkyl is preferably $C_{3-8}$ cycloalkyl($C_{1-4}$)alkyl and is, for example, cyclopropylmethyl, cyclohexylmethyl or cyclohexylethyl.

Heterocyclyl rings are not aromatic and preferably contain from 3 to 8, especially from 3 to 6, atoms selected from the group comprising carbon, oxygen, nitrogen or silicon. It is preferred that the rings contain 1, 2 or 3 heteroatoms. Heterocyclyl rings are, for example, piperidine, morpholine or pyrrolidine; and are, preferably, optionally substituted by hydroxy, alkoxy, alkyl, aryl or arylalkyl groups.

Heteroaryl includes aromatic 5 or 6 membered rings comprising one or more (preferably 1, 2 or 3) heteroatoms (preferably nitrogen, oxygen or sulphur). Heteroaryl is, for example, pyridine, pyrimidine, triazine (1,2,3-, 1,2,4- or 1,3,5-), pyrrole, quinoline or isoquinoline.

Heteroarylalkyl is preferably heteroaryl($C_{1-4}$)alkyl and is, for example, pyrid-2-ylmethyl or pyrid-4-ylmethyl.

Heteroaryloxyalkyl is preferably heteroaryloxy($C_{1-4}$) alkyl and is, for example, pyrid-2-yloxymethyl or pyrid-4-yloxymethyl.

When $R^3$, $R^4$, $R^7$ or $R^{11}$ joins with $R^5$ to form a bridge, optionally substituted $C_{1-3}$ alkyl is especially $C_{1-3}$ optionally substituted with alkyl or phenyl (for example the bridge is $CH_2$, $CH_2CH_2$, $CH(CH_3)CH_2$ or $(CH_2)_3$) and optionally substituted silyl is especially di($C_{1-4}$ alkyl)silyl (such as $(CH_3)_2Si$), diarylsilyl (such as $(C_6H_5)_2Si$) or monoarylmono($C_{1-4}$ alkyl)silyl (such as $(CH_3)(C_6H_5)Si$). The bridge formed is especially $CH_2CH_2$ or $(CH_3)_2Si$.

All aryl and heteroaryl groups are optionally substituted by one or more substituents. Preferred substituents are halogen, hydroxy, mercapto, $C_{1-8}$ alkyl (especially methyl or ethyl), $C_{1-8}$ alkoxy (especially methoxy), $C_{1-4}$ alkylthio (especially methylthio), hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, optionally substituted methylenedioxy or ethylenedioxy (for example optionally substituted by alkyl) or —NR'R", in which R' and R" are independently hydrogen, $C_{1-4}$ alkyl, $C_{3-6}$ cycloalkyl, $C_{3-6}$ cycloalkyl($C_{1-4}$)alkyl, phenyl or benzyl, the phenyl and benzyl groups being optionally substituted with $C_{1-4}$ alkyl or $C_{1-4}$ alkoxy.

In another aspect the present invention provides a compound of formula (Ia) wherein $R^1$ and $R^2$ are different and are trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ and $R^2$ join to form an asymmetrically substituted $C_{3-8}$ cycloalkyl, $C_{3-8}$ cycloalkenyl or $C_{3-8}$ heterocyclyl ring optionally substituted with hydroxy, trialkylsilyl, alkyl, alkoxy, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^3$, $R^4$, $R^5$, $R^6$ and $R^7$ are the same or different and are selected from the substituents already recited for $R^1$ and $R^2$; or $R^3$ and $R^4$ or $R^5$ and $R^6$ or both join to form an optionally substituted saturated or unsaturated ring optionally comprising one or more heteroatoms; or $R^4$, $R^5$, $R^6$ and $R^7$ may also be, independently, hydrogen; or $R^3$, $R^4$ or $R^7$ joins with $R^5$ to form an optionally substituted $C_{1-3}$ alkyl or optionally substituted silyl bridge; $X^1$ and $X^2$ are, independently, groups which are removable during a chemical reaction; and M is titanium, zirconium or hafnium.

In yet another aspect the present invention provides a compound of formula (Ia) wherein $R^1$ and $R^2$ are different and are trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ and $R^2$ join to form an asymmetrically substituted $C_{3-8}$ cycloalkyl, $C_{3-8}$ cycloalkenyl or $C_{3-8}$ heterocyclyl ring optionally substituted with trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^3$, $R^4$, $R^5$ and $R^6$ are the same or different and are selected from the substituents already recited for $R^1$ and $R^2$, or, $R^3$ and $R^4$ or $R^5$ and $R^6$ join to form an optionally substituted saturated or unsaturated ring optionally comprising one or more heteroatoms; or $R^4$, $R^5$ and $R^6$ may also be, independently, hydrogen; $R^7$ is hydrogen or alkyl; or $R^3$, $R^4$ or $R^7$ joins with $R^5$ to form an optionally substituted $C_{1-3}$ alkyl or optionally substituted silyl bridge; $X^1$ and $X^2$ are, independently, groups which are removable during a chemical reaction; and M is titanium, zirconium or hafnium.

In another aspect the present invention provides a compound of formula (Ia) in which $R^3$ and $R^4$ or $R^5$ and $R^6$ join to form an optionally substituted unsaturated (for example aromatic) or, preferably, saturated ring. The ring optionally comprises one or more heteroatoms (such as nitrogen), but is preferably carbocyclic.

In a further aspect the present invention provides a compound of formula (Ia) in which $R^3$ and $R^4$ join together to form (in conjunction with the cyclopentadiene ring to which they are attached) a 6 membered non-aromatic carbocyclic ring.

In yet another aspect the present invention provides a compound of formula (Ia) wherein $R^3$ is $C_{1-4}$ alkyl (especially methyl), $R^4$ is hydrogen or $C_{1-4}$ alkyl (especially methyl or tert-butyl), or $R^3$ and $R^4$ join together to form (in conjunction with the cyclopentadiene ring to which they are attached) a 5, 6 or 7 membered carbocyclic ring (such as a 6 membered aromatic ring), and $R^7$ is hydrogen or $C_{1-4}$ alkyl (such as methyl or tert-butyl).

In a further aspect the present invention provides a compound of formula (Ia) wherein $R^1$ is $C_{1-4}$ alkyl (such as iso-propyl or tert-butyl), phenyl, tri($C_{1-4}$)alkylsilyl (such as trimethylsilyl) or phenyl($C_{1-4}$)alkyl (such as 2-phenylprop-2-yl); and $R^2$ is $C_{1-4}$ alkyl (such as methyl).

In a still further aspect the present invention provides a compound of formula (Ia) wherein $R^1$ and $R^2$ join to form an asymmetrically substituted $C_{3-8}$ cycloalkyl ring (such as cyclopropyl, cyclopentyl or cyclohexyl) optionally substituted with alkyl (such as methyl, ethyl, propyl, iso-propyl, n-butyl, iso-butyl, sec-butyl, tert-butyl) or phenylalkyl (such as benzyl, 1-phenyleth-1-yl, 2-phenyleth-1-yl, 2-phenylprop-2-yl, 1-phenylprop-2-yl or 1-phenyl-2-methylprop-2-yl).

In another aspect the present invention provides a compound of formula (Ia) in which $R^7$ is hydrogen.

In a still further aspect the present invention provides a compound of formula (Ia) wherein $R^1$ and $R^2$ join to form an asymmetrically substituted $C_{3-8}$ cycloalkyl ring (such as cyclopropyl, cyclopentyl or cyclohexyl) optionally substituted with alkyl (such as methyl, ethyl, propyl, iso-propyl, n-butyl, iso-butyl, sec-butyl, tert-butyl) or phenylalkyl (such as benzyl, 1-phenyleth-1-yl, 2-phenyleth-1-yl, 2-phenylprop-2-yl, 1-phenylprop-2-yl or 1-phenyl-2-methylprop-2-yl); $R^3$ and $R^4$ join together to form (in conjunction with the cyclopentadiene ring to which they are attached) a 6 membered non-aromatic carbocyclic ring; $R^5$, $R^6$ and $R^7$ are all hydrogen; and $X^1$ and $x^2$ are, independently, chlorine or bromine.

In another aspect the present invention provides a compound of formula (II) or (II') or an enantiomer thereof, wherein $R^5$ is hydrogen or $C_{1-4}$ alkyl (especially methyl); M is zirconium, titanium or hafnium (but is preferably zirconium); $Y^1$ is $C_{1-4}$ alkyl (especially methyl, iso-propyl or tert-butyl), tri($C_{1-4}$)alkylsilyl (especially trimethylsilyl) or phenyl($C_{1-4}$)alkyl (especially 2-phenylprop-2-yl); $Y^2$, $Y^3$, $Y^4$, $Y^5$, $Y^6$ and $Y^7$ are all hydrogen; $Y^8$ and $Y^9$ are, independently, hydrogen or $C_{1-4}$ alkyl (especially methyl or iso-propyl); and $Y^{10}$ is hydrogen, $C_{1-4}$ alkyl (especially methyl or iso-propyl) or tri($C_{1-4}$ alkyl)silyl (especially trimethylsilyl).

In a further aspect the present invention provides a compound of formula (Ib), wherein $X^1$ and $X^2$ are, independently, groups which are removable during a chemical reaction; M is titanium, zirconium or hafnium; $R^3$ and $R^8$ or $R^1$, $R^3$ and $R^8$ join to form an optionally substituted non-aromatic ring system optionally comprising one or more heteroatoms; or $R^1$ and $R^2$ are different and are hydrogen, trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; one of $R^4$ and $R^{11}$ must be hydrogen the other being selected from the substituents already recited for $R^2$ apart from hydrogen; $R^5$, $R^6$ and $R^7$ are the same or different and are selected from the substituents already recited for $R^2$; or, one or more of $R^4$ or $R^{11}$ (whichever is not hydrogen) and $R^7$ or $R^5$ and $R^6$ join to form an optionally substituted saturated or unsaturated ring optionally comprising one or more heteroatoms; or $R^3$, $R^7$ or $R^4$ or $R^{11}$ (whichever is not hydrogen) joins with $R^5$ to form an optionally substituted $C_{1-3}$ alkyl bridge or optionally substituted silyl bridge. Examples compounds of formula (Ib) are compounds of formulae (IIa)–(IIg), wherein $R^9$ and $R^{10}$ are, independently, hydrogen or alkyl, and other variables are as defined earlier in this paragraph.

The ring system formed when $R^3$ and $R^8$ or $R^1$, $R^3$ and $R^8$ join is, preferably, a mono- or bi-cyclic ring system (such as the ring systems shown in formulae (IIa)–(IIg)). Preferred substituents on the ring system are alkyl, aryl or arylalkyl. Preferred heteroatoms in the ring system are oxygen, sulphur or nitrogen. When it is present, it is preferred that the nitrogen atom is optionally substituted by alkyl.

In another aspect the present invention provides a compound of formula (Ib), wherein $X^1$ and $X^2$ are, independently, groups which are removable during a chemical reaction; M is titanium, zirconium or hafnium; $R^3$ and $R^8$ or $R^1$, $R^3$ and $R^1$ join to form an optionally substituted non-aromatic ring system optionally comprising one or more heteroatoms; or $R^1$ and $R^2$ are different and are hydrogen, trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^4$ is hydrogen; $R^{11}$ is selected from the substituents already recited for $R^2$ apart from hydrogen; $R^5$, $R^6$ and $R^7$ are the same or different and are selected from the substituents already recited for $R^2$; or, one or more of $R^{11}$ and $R^7$ or $R^5$ and $R^6$ join to form an optionally substituted saturated or unsaturated ring optionally comprising one or more heteroatoms; or $R^3$, $R^7$ or $R^{11}$ joins with $R^5$ to form an optionally substituted $C_{1-3}$ alkyl bridge or optionally substituted silyl bridge.

In yet another aspect the present invention provides a compound of formula (Ib), wherein $X^1$ and $X^2$ are, independently, groups which are removable during a chemical reaction; M is titanium, zirconium or hafnium; $R^3$ and $R^8$ or $R^1$, $R^3$ and $R^8$ join to form an optionally substituted non-aromatic ring system optionally comprising one or more heteroatoms, or $R^1$ and $R^2$ are different and are hydrogen, trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^{11}$ is hydrogen; $R^4$ is selected from the substituents already recited for $R^2$ apart from hydrogen; $R^5$, $R^6$ and $R^7$ are the same or different and are selected from the substituents already recited for $R^2$; or, one or more of $R^4$ and $R^7$ or $R^5$ and $R^6$ join to form an optionally substituted saturated or unsaturated ring optionally comprising one or more heteroatoms; or $R^3$, $R^7$ or $R^4$ joins with $R^5$ to form an optionally substituted $C_{1-3}$ alkyl bridge or optionally substituted silyl bridge.

In a still further aspect the present invention provides a compound of formula (Ib) wherein when $R^{11}$ is hydrogen $R^4$ and $R^7$ join together to form (in conjunction with the cyclopentadiene ring to which they are attached) a 6 membered non-aromatic carbocyclic ring; or when $R^4$ is hydrogen $R^{11}$ and $R^7$ join together to form (in conjunction with the cyclopentadiene ring to which they are attached) a 6 membered non-aromatic carbocyclic ring.

In another aspect the present invention provides a compound of formula (Ia), or an enantiomer thereof, wherein $X^1$ and $X^2$ are halogen (especially chlorine); M is titanium or zirconium; one of $R^4$ and $R^{11}$ is hydrogen the other being $C_{1-6}$ alkyl (especially methyl, ethyl or tert-butyl) or phenyl; $R^7$ is hydrogen, $C_{1-6}$ alkyl (especially methyl, ethyl or tert-butyl) or phenyl; or $R^4$ or $R^{11}$ (whichever is not hydrogen) and $R^7$ join together to form (in conjunction with the cyclopentadiene ring to which they are attached) a 6-membered non-aromatic carbocyclic ring.

In yet another aspect the present invention provides a compound of formula (I) (especially a compound of formula (Ia) or (Ib)) in which $R^5$ and $R^6$ are both hydrogen.

In yet another aspect the present invention provides a compound of formula (I) (especially a compound of formula (Ia) or (Ib)) in which $X^1$ and $X^2$ are, independently, halogen (preferably chlorine or bromine), alkyl, alkoxy, alkenyl, alkynyl, cycloalkyl, aryl or aryloxy.

Alkenyl and alkynyl groups have straight or branched chains. They preferably contain from 2 to 10, especially from 2 to 6 (such as 2 to 4) carbon atoms, and are, for example, vinyl, allyl or propargyl. Alkenyl and alkynyl groups are optionally substituted by aryl.

In yet another aspect the present invention provides a compound of formula (I) (especially a compound of formula (Ia) or (Ib)) in which $X^1$ and $X^2$ are, independently, halogen.

In a further aspect the present invention provides a compound of formula (I) (especially a compound of formula (Ia) or (Ib)) in which M is zirconium.

The compounds of Tables I to XXVI illustrate the invention.

TABLE I

All the compounds of Table I are of formula (II) wherein M is zirconium and $R^5$ is hydrogen.

| Compound No. | $Y^1$ | $Y^2$ | $Y^3$ | $Y^4$ | $Y^5$ | $Y^6$ | $Y^7$ | $Y^8$ | $Y^9$ | $Y^{10}$ |
|---|---|---|---|---|---|---|---|---|---|---|
| 1 | $Pr^i$ | H | H | H | H | H | H | $CH_3$ | H | H |
| 2 | $Pr^i$ | H | H | H | H | H | H | H | $CH_3$ | H |
| 3 | Bn | H | H | H | H | H | H | $CH_3$ | H | H |
| 4 | $Bu^t$ | H | H | H | H | H | H | $CH_3$ | H | H |
| 5 | $Pr^i$ | H | H | H | H | H | H | $Pr^i$ | H | H |
| 6 | Bn | H | H | H | H | H | H | $Pr^i$ | H | H |
| 7 | $Bu^t$ | H | H | H | H | H | H | $Pr^i$ | H | H |
| 8 | $Pr^i$ | H | H | H | H | H | H | H | H | H |
| 9 | Bn | H | H | H | H | H | H | H | H | H |
| 10 | $Bu^t$ | H | H | H | H | H | H | H | H | H |
| 11 | $CH_3$ | H | H | H | H | H | H | H | H | $CH_3$ |
| 12 | $Pr^i$ | H | H | H | H | H | H | H | H | $Pr^i$ |
| 13 | SM | H | H | H | H | H | H | H | H | SM |

$Pr^i = (CH_3)_2HC$
$Bu^t = (CH_3)_3C$
$Bn = C_6H_5(CH_3)_2C$
$SM = Si(CH_3)_3$

TABLE II

Table II comprises 13 compounds of formula (II) wherein $R^5$ is hydrogen and M is titanium and $Y^1$, $Y^2$, $Y^3$, $Y^4$, $Y^5$, $Y^6$, $Y^7$, $Y^8$, $Y^9$ and $Y^{10}$ have the values listed for the correspondingly numbered compound in Table I.

TABLE III

Table III comprises 13 compounds of formula (II) wherein $R^5$ is hydrogen and M is hafnium and $Y^1$, $Y^2$, $Y^3$, $Y^4$, $Y^5$, $Y^6$, $Y^7$, $Y^8$, $Y^9$ and $Y^{10}$ have the values listed for the correspondingly numbered compound in Table I.

TABLES IV TO VI

Each of Tables IV to VI comprises 13 compounds of formula (I) wherein $R^5$ is methyl and M, $Y^1$, $Y^2$, $Y^3$, $Y^4$, $Y^5$, $Y^6$, $Y^7$, $Y^8$ $Y^9$ and $Y^{10}$ have the values listed for the correspondingly numbered compounds of Tables I to III respectively.

TABLES VII TO XII

Each of Tables VII to XII comprises 13 compounds. The compounds of these Tables are the enantiomers of the compounds of formula (II) of Tables I to VI respectively wherein $R^5$, M, $Y^1$, $Y^2$, $Y^3$, $Y^4$, $Y^5$, $Y^6$, $Y^7$, $Y^8$, $Y^9$ and $Y^{10}$ have the values listed for the correspondingly numbered compounds of Tables I to VI.

TABLES XIII TO XVIII

Each of Tables XIII to XVIII comprises 13 compounds. The compounds of these Tables are compounds of formula (II') wherein $R^5$, M, $Y^1$, $Y^2$, $Y^3$, $Y^4$, $Y^5$, $Y^6$, $Y^7$, $Y^8$, $Y^9$ and $Y^{10}$ have the values listed for the correspondingly numbered compounds of Tables I to VI.

TABLES XIX TO XXIV

Each of Tables XIX to XXIV comprises 13 compounds. The compounds of these Tables are the enantiomers of the compounds of formula (II') of Tables XIII to XVIII respectively wherein $R^5$, M, $Y^1$, $Y^2$, $Y^3$, $Y^4$, $Y^5$, $Y^6$, $Y^7$, $Y^8$, $Y^9$ and $Y^{10}$ have the values listed for the correspondingly numbered compounds of Tables XIII to XVIII.

TABLE XXV

Table XV comprises compounds of formula (IIa) wherein $X^1$ and $X^2$ are both chlorine.

| Compound No. | $R^4$ | $R^7$ | $R^{11}$ | M | $R^5$ | $R^6$ |
|---|---|---|---|---|---|---|
| 1 | $CH_3$ | H | H | Zr | H | H |
| 2 | $CH_3$ | H | H | Ti | H | H |
| 3 | $CH_3$ | H | H | Zr | $CH_3$ | H |
| 4 | $CH_3$ | H | H | Ti | $CH_3$ | H |
| 5 | $CH_2CH_3$ | H | H | Zr | H | H |
| 6 | $CH_2CH_3$ | H | H | Ti | H | H |
| 7 | $CH_2CH_3$ | H | H | Zr | $CH_3$ | H |
| 8 | $CH_2CH_3$ | H | H | Ti | $CH_3$ | H |
| 9 | H | H | $CH_3$ | Zr | H | H |
| 10 | H | H | $CH_3$ | Ti | H | H |
| 11 | H | H | $CH_3$ | Zr | $CH_3$ | H |
| 12 | H | H | $CH_3$ | Ti | $CH_3$ | H |
| 13 | $CH_3$ | $CH_3$ | H | Zr | H | H |
| 14 | $CH_3$ | $CH_3$ | H | Ti | H | H |
| 15 | H | $CH_3$ | $CH_3$ | Zr | $CH_3$ | H |
| 16 | H | $CH_3$ | $CH_3$ | Ti | $CH_3$ | H |
| 17 | —$(CH_2)_4$— | | H | Zr | H | H |
| 18 | H | —$(CH_2)_4$— | | Ti | H | H |
| 19 | H | —$(CH_2)_4$— | | Zr | $CH_3$ | H |
| 20 | H | —$(CH_2)_4$— | | Ti | $CH_3$ | H |
| 21 | H | —$(CH_2)_4$— | | Zr | H | H |
| 22 | —$(CH_2)_4$— | | H | Ti | H | H |
| 23 | —$(CH_2)_4$— | | H | Zr | $CH_3$ | H |
| 24 | —$(CH_2)_4$— | | H | Ti | $CH_3$ | H |
| 25 | $C_6H_5$ | H | H | Zr | H | H |
| 26 | $C_6H_5$ | H | H | Ti | H | H |

TABLE XXVI

Tables XXVI comprises 26 compounds. The compounds of this Table are the enantiomers of the compounds of formula (IIa) of Table XXV wherein M, $R^4$, $R^5$, $R^6$, $R^7$ and $R^{11}$ have the values listed for the correspondingly numbered compounds of Table XXV.

The compounds of formula (I) can be prepared by one of the following procedures. References to compounds of formula (III) or (V) include all double bond isomers within the cyclopentadiene ring.

The compounds of formula (I) can be prepared by deprotonating a compound of formula (III) (for example with a butyllithium) in a suitable solvent (such as tetrahydrofuran) and reacting the product obtained with a compound of formula (IV) (wherein L is a suitable leaving group such as a halogen atom). Alternatively, the compounds of formula (I) can be prepared by deprotonating a compound of formula (V) (for example with a butyllithium) in a suitable solvent (such as tetrahydrofuran) and reacting the product obtained with a compound of formula (VI) (wherein L is a suitable leaving group such as a halogen atom).

The compounds of formula (I) can be prepared by reacting a trialkylsilyl or trialkylstannyl derivative of a compound of formula (III) with a compound of formula (IV) (wherein L is a suitable leaving group such as a halogen atom) in a suitable solvent (such as tetrahydrofuran). Alternatively, the compounds of formula (I) can be prepared by reacting a trialkylsilyl or trialkylstannyl derivative of a compound of formula (V) with a compound of formula (VI) (wherein L is a suitable leaving group such as a halogen atom) in a suitable solvent (such as tetrahydrofuran).

Alternatively, when $R^3$ and $R^4$ join to form a saturated, non-aromatic, carbocyclic ring, a compound of formula (I) can be prepared hydrogenating a compound of formula (I) wherein $R^3$ and $R^4$ join to form an aromatic ring under suitable conditions (such as with hydrogenation at room temperature, 1 bar (1 atmosphere; 760 mm Hg) using a suitable catalyst (such as platinum oxide) in a suitable solvent (such as dichloromethane)).

Alternatively, a compound of formula (I) wherein M is titanium can be prepared by carrying out any of the above processes on a titanium (III) derivative followed by oxidation.

Certain compounds of formula (I) (such as those wherein $R^3$ and $R^4$ form an saturated ring, and M is titanium) are preferably prepared by chemically modifying the nature the ligand incorporating $R^3$ and $R^4$ whilst the ligand is attached to zirconium, removing the ligand from zirconium (preferably by reacting the zirconium compound (which is preferably in solution (for example in a solution of an aromatic solvent, such as benzene)) with a suitable base (such as a hydroxide, for example sodium hydroxide)) and then attaching the ligand to a compound of formula (IV) using the methodology described above.

Compounds of formula (IV) are either know in the literature or can be prepared by suitable modification of literature methods (such as the method of Lund, E. C. et al in Organometallics (1990) 9 2426–7). Compounds of formula (III) are either known in the literature or can be prepared by suitable modification of literature methods (such as the method of Erker, G. in Journal American Chemical Society (1993) 115 4590). Compounds of formula (VI) are either known in the literature or can be prepared by suitable modification of literature methods (such as a combination of the methods referred to earlier). Compounds of formula (V) are either known in the literature or can be prepared by suitable modification of literature methods.

In further aspects the present invention comprises processes for preparing compounds of formulae (I) (especially compounds of formula (Ia) or (Ib)) and (II) and enantiomers thereof.

The compounds of the invention (especially the compounds of formulae (Ia) or (Ib)) can be used as catalysts in a variety of different industrial processes from which chiral products are required. Examples of such processes are hydride transfers (such as hydrogenations of chain or cyclic alkenes, imines or enarines), the preparation of secondary alcohols from ketones, the catalytic asymmetric carbomagnesiation or carboalumination of alkenes (resulting in good enantiomeric excesses), the intermolecular dimerisation of alkenes, the intramolecular co-cyclisation of 1,n-dienes, the intramolecular co-cyclisation/elimination of an alkene with an alkene carrying an allylic leaving group, the alkylation of heteroaromatic (such as pyridines, quinolines or isoquinolines) with alkenes or the Ziegler Natta type polymerisations or oligomerisations of alkenes.

Alternatively, the compounds of the invention (especially the compounds of formulae (Ia) or (Ib)) can be used stoichiometrically in a variety of different industrial processes from which chiral products are required. Examples of such processes are trapping of zirconocene $\eta^2$-imine complexes, cocyclisation of enynes or dienes, addition of in situ formed zirconocene $\eta^2$-alkene complexes to alkenes, alkynes or ketones, addition of in situ formed zirconocene $\eta^2$-benzyne complexes to alkenes, aldehydes or imines, or addition of in situ formed zirconocene $\eta^2$-alkyne complexes to alkenes, aldehydes or imines.

An important advantage of using the compounds of formulae (Ia) or (Ib) in the processes given above is that the compounds of formulae (Ia) or (Ib) are recoverable at the end of such processes and do not lose their chirality during the course of the process in which they are used.

The compounds of the invention (especially the compounds of formulae (Ia) or (Ib)) can be used in the above processes in free molecular form or bound to a polymer support. For example, a compound of formula (Ia) can be attached to a polymer support through either cyclopentadiene ring (especially the ring carrying the substituents $R^5$ and $R^6$), a compound of formula (II) or (II') having at least one of $Y^3$ $Y^4$, $Y^5$, $Y^6$, $Y^7$, $Y^8$, $Y^9$, or $Y^{10}$ as alkyl, can be attached to a polymer support through said alkyl group. Suitable polymer supports include polymers derived from cross linked polystyrene. Examples of compounds of the invention bound to a polymer support are presented as structures (A), (B) and (C). In these structures the encircled letter P denotes a polymer support. A compound of formula (Ib) can, by analogy, be attached to a polymer support through either a cyclopentadiene ring or through an alkyl group.

The following Examples illustrate the invention. All NMR data is expressed in ppm from tetramethylsilane. Throughout the Examples the following abbreviations are used:

| | |
|---|---|
| THF = tetrahydrofuran | NMR = Nuclear Magnetic Resonance |
| ppm = parts per million | s = singlet |
| d = doublet | m = multiplet |
| t = triplet | q = quartet |
| dd = doublet of doublets | dt = doublet of triplets |
| brs = broad singlet | ddd = doublet of doublet of doublets |
| mp = melting point | DME = dimethoxyethane |
| eq = equivalents | |
| HMPA = hexamethylphosphoramide $((CH_3)_2N)_3PO$ | |
| $CpZrCl_3$ = cyclopentadienyl zirconium trichloride | |

$CpZrCl_3$.DME may be prepared by the method of Lund, E. C. et al in Organometallics (1990) 9 2426–7.

EXAMPLE 1

This Example illustrates the preparation of (cyclopentadienyl)(1-[(1'S,2'S,5'R)-2'-isopropyl-5'-methylcyclohexyl]-4,5,6,7-tetrahydroindenyl)zirconium dichloride (Compound No. 1 in Table VII).

(+)-3-[(1'S,2'S,5'R)-2'-isoPropyl-5'-metliylcyclohexyl]indene (1.017 g, 4 mmol, 1 eq) was dissolved in THF (10 ml) and cooled to −78° C. n-Butyllithium (1.6 ml of 2.5 M solution in hexanes, 4 mmol, 1 eq) was added and the orange solution stirred at room temperature for two hours. This solution was then added to a suspension of $CpZrCl_3$.DME in THF (10 ml) at room temperature. The bright yellow solution was stirred overnight before the solvent was removed in vacuo and the residue redissolved in dichloromethane (10 ml). Platinum oxide (90 mg, 0.4 mmol, 10%) was added and the mixture was stirred under an atmosphere of hydrogen gas (1 bar) overnight. The colourless solution was filtered through CELITE™ and the solvent removed to furnish the title material as a pale solid (738 mg, 38%). The product was recrystallised from hot toluene to furnish clear block crystals. mp 237–238° C.

$^1$H NMR (300 MHz; $CDCl_3$): δ 6.46 (d,1H), 6.44(s,5H), 5.58(d,J=2.9 Hz,1H), 3.07(m,1H), 2.88(m,2H), 1.00–1.95 (m,18H), 0.98(d,J=6.6 Hz,3H), 0.73(d,J=0.38(d,J=6.9 Hz,3H)ppm.

$^{13}$C NMR (75.5 MHz; $CDCl_3$): δ 137.8(s), 137.2(s), 131.7(s), 114.8(d), 110.0(d), 102.9(d), 47.6(d), 39.4(t), 36.4 (d), 33.6(t), 29.0(d), 28.9(d), 24.9(t), 24.5(t), 24.1(q), 22.5 (t), 22.2(t), 22.1(t), 21.9(q), 18.5(q)ppm.

EXAMPLE 2

This Example illustrates the preparation of (cyclopentadienyl)(1-[(1'R,2'R,5'S)-2'-isopropyl-5'-methylcyclohexyl]-4,5,6,7-tetrahydroindenyl)zirconium dichloride (Compound No. 1 of Table I).

Indene (6.156 g, 53 mmol, 11.1 eq) was dissolved in THF (50 ml). The solution was cooled to −78° C. and n-butyllithium (21.2 ml, of 2.5M solution in hexanes, 53 mmol, 1.1 eq) added. The orange solution was allowed to warm to room temperature and was stirred for one hour. After recooling to −78° C., (+)-(1S,2R,5S)-2-isopropyl-5-methylcyclohexan-1-ol p-toluenesulphonate ((+) menthol tosylate; 15.0 g, 48 mmol, 1 eq) in THF (50 ml) was added followed by HMPA (17.2 g, 96 mmol, 2 eq). The solution was allowed to warm slowly to room temperature and was stirred overnight. Water (100 ml) was added and the product extracted into diethylether (3×75 ml). After drying over $MgSO_4$ the solvent was removed in vacuo. The product was purified by column chromatography (eluant petroleum ether) followed by Kugelrohr distillation (155° C., 0.4 mbar) to yield (−)-3-[(1'R,2'R,5'S)-2'-isopropyl-5'-methylcyclohexyl]indene as a white crystalline solid (1.036 g, 8.5%).

$^1$H NMR (300 MHz; $CDCl_3$): δ 7.56 (d,J=7.5 Hz,1H), 7.48 (d,J=8.1 Hz,1H), 7.40(t,J=7.5 Hz,1H), 7.29(t,J=7.5 Hz,1H), 6.46(s,1H), 3.45(s,2H), 1.33–1.92(m,9H), 1.02(d, J=6.6 Hz,3H), 0.88(d,J=6.6 Hz,3H), 0.82(d,J=6.6 Hz,3H) ppm.

$^{13}$C NMR (75.5 MHz; $CDCl_3$): δ 146.8(s), 144.8(s), 143.9(s), 129.6(d), 126.2(d), 124.5(d), 123.8(d), 119.0(d), 47.8(d), 39.8(t), 38.6(t), 35.8(t), 34.3(d), 30.3(d), 27.5(t), 27.0(d), 22.6(q), 21.8(q), 21.6(q)ppm.

(−)-3-[(1'R,2'R,5'S)-2'-isoPropyl-5'-methylcyclohexyl]indene (1.017 g, 4 mmol, 1 eq) was dissolved in THF (10 ml) and cooled to −78° C. n-Butyllithium (1.6 ml of 2.5 M solution in hexanes, 4 mmol, 1 eq) was added and the orange solution stirred at room temperature for two hours. This solution was then added to a suspension of $CpZrCl_3$.DME in THF (10 ml) at room temperature. The bright yellow solution was stirred overnight before the solvent was removed in vacuo and the residue redissolved in dichloromethane (10 ml). Platinum oxide (90 mg, 0.4 mmol, 10%) was added and the mixture was stirred under an atmosphere of hydrogen gas (1 bar) overnight. The colourless solution was filtered through CELITE™ and the solvent removed to furnish the title material as a pale solid (0.521 g, 27%). The product was recrystallised from hot toluene. mp 237–238° C.

EXAMPLE 3

This Example illustrates the preparation of (cyclopentadienyl)(1-[(1'-R,2'R,5'R)-2'-isopropyl-5'-methylcyclohexyl]-4,5,6,7-tetrahydroindenyl)zirconium dichloride (Compound No. 2 of Table I).

(+)-3-[(1'R,2'R,5'R)-2'-isoPropyl-5'-methylcyclohexyl]indene (1.017 g, 4 mmol, 1 eq) was dissolved in THF (10 ml) and cooled to −78° C. n-Butyllithium (1.6 ml of 2.5 M solution in hexanes, 4 mmol, 1 eq) was added and the orange solution stirred at room temperature for two hours. This solution was added to a suspension of $CpZrCl_3$.DME in THF (10 ml) at room temperature. The yellow solution was stirred overnight before the solvent was removed in vacuo and the residue redissolved in dichloromethane (10 ml). Platinum oxide (90 mg, 0.4 mmol, 10%) was added and the mixture was stirred under an atmosphere of hydrogen gas (1 bar) overnight. The colourless solution was filtered through CELITE™ and the solvent removed to furnish the title material as a pale solid (641 mg, 33%). mp 209–212° C.

$^1$H NMR (300 MHz; $CDCl_3$): δ 6.42 (s,5H), 6.13(d,J=2.6 Hz, 1H), 5.63(d,J=2.8 Hz,1H), 2.73–3.00(m,3H), 2.51(m, 2H), 1.10–1.65(m,24H), 0.94(d,J=6.1 Hz,3H), 0.85(d,J=6.6 Hz,3H), 0.31(d,J=6.2 Hz,3H)ppm.

$^{13}$C NMR (75.5 MHz; $CDCl_3$): δ 139.9(s), 138.5(s), 129.9(s), 114.8(d), 106.6(d), 102.3(d), 41.7(d), 40.6(d), 35.3

(t), 32.6(d), 30.7(t), 29.4(t), 25.6(d), 24.9(t), 24.4(q), 23.8(t), 23.2(q), 22.6(t), 21.8(t), 21.7(q)ppm.

EXAMPLE 4

This Example illustrates the preparation of (cyclopentadienyl)(1-[(1'S,2'S,5')-2'-isopropyl-5'-methylcyclohexyl]-4,5,6,7-tetrahydroindenyl) titanium dichloride (Compound No. 1 in Table VIII).

Step 1: Preparation of (+)-3[(1'S,2'S,5'R)-2'-isopropyl-5'-methylcyclohexyl]4,5,6,7-tetrahydroindene {3-Neomenthyltetrahydroindene}.

(Cyclopentadienyl)(neomenthyltetrahydroindenyl) zirconium dichloride (1.058 g, 2.2 mmol, prepared as in Example 1) was dissolved in benzene (10 mL) and stirred with sodium hydroxide (10 ml, 5 M) under an inert atmosphere. After 2 hours the organic phase was separated and the aqueous phase extracted with ethyl acetate (4×50 ml). The combined organics were dried and the solvent removed to yield a yellow oil. The product was purified by column chromatography (eluant petroleum ether) to furnish the product of step 1 as a white low melting solid (0.426 g, 83%). mp 39–41° C. (crystallised from pentane).

$^1$H NMR (300 MHz; CDCl$_3$): δ 5.95(s,1H), 2.88(s,1H), 2.80(s,1H), 2.34(s,1H), 2.22(s,1H), 0.74–1.90(m,25H); including 1.71('quin.', J=3.0 Hz,1H), 0.89(d, J=6.6 Hz,3H), 0.82(d,J=5.9 Hz,3H), 0.75(d,J=5.9 Hz,3H)ppm. $^{13}$C NMR (75.5 MHz; CDCl$_3$): δ 147.5(s), 139.9(s), 138.7(s), 124.5(d), 47.9(d), 45.2(t), 40.3(t), 35.7(t), 34.3(d), 29.6(d), 26.9(t), 25.9(d), 25.8(t), 24.0(t), 23.4(t), 23.2(t), 22.7(q), 21.6(q), 21.5(q)ppm.

Step 2: Preparation of title compound.

Neomenthyltetrahydroindene (300 mg, 1.2 mmol, 1 equivalent; as prepared in step 1) was dissolved in tetrahydrofuran (6 ml) and cooled in an ice bath. n-Butyllithium (0.48 ml of 2.5 M solution in hexanes, 1.2 mmol, 1 equivalent) was added dropwise and the pale yellow solution stirred at room temperature for 2 hours. This solution was then added to a solution of cyclopentadienyltitanium trichloride (250 mg, 1.14 mmol, 0.95 equivalent) in tetrahydrofuran (6 ml) at −78° C. A red solution was immediately formed. The reaction was allowed to warm slowly to room temperature and the solvent was removed to yield a red solid. The product was purified by column chromatography (eluant benzene) and furnished as a mixture of isomers (0.427 g, 85%). The major isomer could be separated by double recrystallisation from hot toluene.

major isomer (Compound No. 1 in Table VIII):

mp 220–222° C. (recrystallised from toluene);

$^1$H NMR (360 MHz; CDCl$_3$): δ 6.46(s,5H), 6.16(d,J=3.0 Hz,1H), 5.77(d,J=3.0 Hz,1H), 3.35(dt,J=9.2, 3.7 Hz, 1H), 3.15 (dt,J=17.6, 5.6 Hz,1H), 2.75(m,2H), 2.54(dt,J=16.8, 5.6 Hz, 1 H), 2.02(ddd,J=17.6, 9.2, 4.5 Hz, 1H), 1.46–1.90(m, 10H), 1.41(m,1H), 1.19(m,1H), 0.93(d,J=7.1 Hz,3H), 0.89 (d,J=6.7 Hz,3H), 0.61(d,J=6.4 Hz,3H)ppm.

$^{13}$C NMR(90 MHz; CDCl$_3$): δ 141.7(s), 139.8(s), 138.1 (s), 118.6(d), 114.1(d), 109.7(d), 49.3(d), 38.9(d), 34.8(t), 30.7(t), 27.3(d), 26.9(d), 26.7(t), 26.6(t),25.1(t), 24.0(q), 22.1(t), 21.9(t), 21.6(q), 19.8(q)ppm. minor isomer (Compound No. 1 of Table XX):

$^1$H NMR(360 MHz; CDCl$_3$): δ 6.55(d,J=2.6 Hz,1H), 6.49(s,5H), 5.57(d,J=2.7 Hz,1H), 3.07(ddd,J=16.5, 7.0, 4.8 Hz, 1H), 2.93(dt,J=17.3, 6.7 Hz, 1H), 2.75(m,1H), 2.45(dt, J=1.72, 6.3 Hz, 1H), 1.0–2.25(m, 14H), 0.95(d,J=6.9 Hz, 3H), 0.70(d,J=6.6 Hz,3H), 0.45(d,J=6.7 Hz,3H)ppm.

$^{13}$C NMR (90 MHz; CDCl$_3$): δ 144.7(s), 144.2(s), 137.3 (s), 118.4(d), 111.7(d), 106.2(d), 47.2(d), 37.5(t), 36.8(d), 32.7(t), 28.9(d), 28.3(d), 25.9(t), 25.1(t), 23.9(q), 22.3(t), 22.0(t), 21.7(t), 21.3(q), 18.9(q).,1.48(m, 4 H)ppm.

EXAMPLE 5

This Example illustrates the preparation of(η$^5$-(1R,7S)-1,3,10,10-tetramethyltricyclo-[5.2.1.0$^{2,6}$]-deca-2,5-dien-4-yl)(η$^5$-cyclopentadienyl)zirconium dichloride. (Compound No. 1 in Table XIII).

(1R,7S)-1,3,10,10-Tetramethyltricyclo[5.2.1.0$^{2,6}$]-deca-2,5-diene (0.2 g, 1.06 mmol) was dissolved in freshly distilled diethyl ether (30 ml) and cooled to 0° C. before n-butyllithium (0.44 ml, 2.5 M, 1.1 mmol) was added dropwise via a syringe to afford a yellow solution which was stirred for 4 hours at room temperature after which the solution was colourless. The lithium salt solution was added to a slurry of CpZrCl$_3$.DME (0.56 g, 1.59 mmol) in freshly distilled diethyl ether (10 ml) and the reaction mixture stirred at room temperature for 36 hours. The residue was filtered under argon and the filtrate reduced in volume under vacuum to yield a black oil, which was extracted with benzene (30 ml), filtered through a sinter and again reduced in volume to yield a second black oil. The product was extracted from the oil with hot (60° C.) hexane, which upon cooling afforded a dirty yellow precipitate of crude metallocene. The solid was isolated and recrystallised again from hot hexane, giving the title compound in 3.4% yield as an off-white crystalline solid with a 10:1 mixture of exo and endo isomers (15 mg, 0.04 mmol).

$^1$H NMR (CDCl$_3$) 300 MHz: δ/ppm 6.47(s,5H), 6.07(d, J=3 Hz, 1H), 5.76(d,J=3 Hz, 1H), 2.69(d,J=4 Hz, 1H), 2.32(s,3H), 1.22(s,3H), 0.90(s,3H), 0.28(s,3H). In addition the following signals from the minor (exo) isomer (Compound No. 1 in Table XXV) could be distinguished: 6.21(d,J=3 Hz,1H), 5.91(d, J=3 Hz, 1H), 2.96(d,J=4 Hz, 1H).

EXAMPLE 6

This Example illustrates the preparation of (η$^5$-(1R,7S)-1,3,10,10-tetramethyltricyclo-[5.2.1.0$^{2,6}$]-deca-2,5-dien-4-yl)(η$^5$-cyclopentadienyl)titanium dichloride (Compound No. 2 in Table XIII).

(1R,7S)-1,3,10,10-Tetramethyltricyclo[5.2.1.0$^{2,6}$]-deca-2,5-diene (0.2 g, 1.06 mmol) was dissolved in freshly distilled tetrahydrofuran (15 ml) and n-butyllithium (0.44 ml, 2.5 M, 1.1 mmol) was added dropwise via a syringe to afford a yellow solution which was stirred for 4 hours at room temperature. The lithium salt solution was added to a stirred solution of cyclopentadienyl titanium trichloride (0.23 g, 1.05 mmol) in freshly distilled tetrahydrofuran (15 ml) and the reaction mixture stirred at room temperature for 38 hours. The solvent was removed from the reaction mixture under reduced pressure, and the dark red residue was dissolved in choroform (20 ml) in air, and concentrated hydrochloric acid (4 ml) added and stirred for 2 hours. The aqueous phase was washed with chloroform (3×10 ml) and the combined organic layers were dried (MgSO$_4$) and the solvent removed under reduced pressure to yield a black crude residue. Recrystallization of the crude material from a hexane/dichloromethane mixture (approx. 1:1) gave the title compound in 23% yield (90 mg, 0.24 mmol).

$^1$H NMR (CDCl$_3$) 300 MHz: δ 6.55 (s,5H), 6.25(d,J=3 Hz,1H), 5.98(d,J=3 Hz,1H), 2.78(d,J=4 Hz, 1H), 2.52(s,3H), 2.08(m,2H), 1.64(m,1H), 1.44(m,1H), 1.23(s,3H), 0.92(s, 3H), 0.32(s,3H)ppm.

$^{13}$C NMR (CDCl$_3$) 75.5 MHz: δ 162.06, 145.53, 129.44, 128.00, 119.30, 109.85, 70.35, 55.61, 51.37, 32.76, 25.61, 21.32, 20.06, 14.69, 12.81 ppm.

The following Examples illustrate how the compounds of the invention can be used in chemical reactions. Enantiomeric excesses (ee) were measured by Moschers ester analysis, by chiral gas chromatography using a chiral column (such as an Astec A-DA, or MN-CAMAG FS-Hydrodex-β-3P capillary column) or by chiral high pressure liquid chromatography using a chiral column (such as a Chiracel OD-H, OB, or chiralpak AD (Daicel)).

EXAMPLE 7
Preparation of N-Methyl-N-(2-methylthiomethyletherbutyl) aniline.

(Cyclopentadienyl)(1-[(1'S,2'S,5'R)-2'-isopropyl-5'-methylcyclohexyl]-4,5,6,7-tetrahydroindenyl)zirconium dichloride (prepared as in Example 1, 24 mg, 0.05 mmol) was dissolved in a solution of diethylmagnesium (5.5 ml of a 0.73 M solution in diethyl ether, 4.0 mmol). N-Allyl-N-methylaniline (0.147 g, 1 mmol) was added as a solution in THF (1 ml). The resulting mixture was stirred at room temperature for 24 hours. The mixture was cooled to 0° C. and dry $CH_3SSCH_3$ (1 g) in THF (1 ml) was added. The resulting mixture was poured into saturated aqueous ammonium chloride solution (100 ml) and the aqueous was extracted with diethyl ether (3×50 ml). The organic extracts were combined, dried and evaporated in vacuo to leave an oil which was purified by column chromatography (eluant 0.5% diethyl ether in petroleum ether, 2% diethyl ether in petroleum ether finally 100% diethyl ether) to give the title compound as a clear oil (0.137 g, 61%, 52% ee).

$^1$H NMR (300 MHz, $CDCl_3$): 7.26(m,2H), 6.76(d,J=9 Hz,2H), 6.70(tt,J=7.2,1.2 Hz,1H), 3.43(dd,J=14.7,7.8 Hz,1H), 3.23(dd,J=14.7,6.9 Hz,1H), 2.99(s,3H), 2.57(d,J=5.7 Hz,2H), 2.11 (s,3H), 2.04(m,1H), 1.49(m,2H), 0.98(t,J=7.2 Hz,3H) ppm.

$^{13}$C NMR (75.5 MHz, $CDCl_3$): 149.7(s), 129.3(d), 116.1 (d), 112.2(d), 56.4(t), 39.6(d), 38.6(q), 37.0(t), 24.2(t), 16.7 (q), 11.2(q) ppm.

EXAMPLE 8
Preparation of N-(2-methylthiomethyletherbutyl)aniline.

(Cyclopentadienyl)(1-[(1'S,2'S,5'R)-2'-isopropyl-5'-methylcyclohexyl]-4,5,6,7-tetrahydroindenyl)zirconium dichloride (prepared as in Example 1, 19 mg, 0.04 mmol) was dissolved in a solution of diethylmagnesium (5.7 ml of a 1.4 M solution in diethyl ether, 8 mmol). N-Allylaniline (0.266 g, 2 mmol) was added and the resulting mixture was stirred at room temperature overnight. The mixture was cooled to 0° C. and quenched with dry $CH_3SSCH_3$ (1 g) in THF (2 ml). The resulting mixture was poured into saturated aqueous ammonium chloride solution (100 ml) and the aqueous was extracted with diethyl ether (3×50 ml). The organic extracts were combined, dried and evaporated in vacuo to leave an oil which was purified by column chromatography (eluant 2% diethyl ether in petroleum ether) followed by Kugelrohr distillation (70° C., 0.5 mbar) to give the title compound as a clear oil (0.399 g, 95%, 75% ee).

$^1$H NMR (300 MHz, $CDCl_3$): 7.22(m,2H), 6.70(m,3H), 3.23(dd,J=13.0,6.5 Hz,1H), 3.17(dd,J=13.0,6.5 Hz,1H), 2.63(dd,J=12.9,5.7 Hz,1H), 2.58(dd,J=12.7,6.5 Hz), 2.13(s, 3H), 1.87(sept,J=6.2 Hz,1H), 1.52(quin,J=6.2 Hz,1H), 0.99 (t,J=5.0 Hz,3H) ppm.

$^{13}$C NMR (67.5 MHz, $CDCl_3$): 148.5(s), 129.4(d), 117.3 (d), 112.8(d), 46.8(t), 39.2(d), 37.4(t), 24.7(t), 16.6(q), 11.2 (q) ppm.

In a similar fashion (cyclopentadienyl)-(1-[(1'R,2'R,5'S)-2'-isopropyl-5'-methyl cyclohexyl]-4,5,6,7-tetrahydroindenyl)zirconium dichloride (as prepared in Example 2) gave the title compound in 52% yield and 79% ee; and (cyclopentadienyl)-(1-[(1'R,2'R,5'R)-2'-isopropyl-5'-methylcyclohexyl]-4,5,6,7-tetrahydroindenyl)zirconium dichloride gave the title compound in 73% yield and 36% ee.

EXAMPLE 9
Preparation of 2-Methylbutanol.

(Cyclopentadienyl)(1-[(1'S,2'S,5'R)-2'-isopropyl-5'-methylcyclohexyl]-4,5,6,7-tetrahydroindenyl)zirconium dichloride (prepared as in Example 1, 24 mg, 0.05 mmol) was dissolved in a solution of diethylmagnesium (5.5 ml of a 0.73 M solution in diethyl ether, 0.04 mmol). Allylalcohol (0.058 g, immol) was added and the resulting mixture was stirred at room temperature overnight. The mnixture quenched by pouring it into a mixture of ice and ammonium chloride solution. The aqueous was extracted with diethyl ether (3×50 ml). The organic extracts were combined, dried and evaporated at atmospheric pressure to leave a crude product. The crude product was added to camphor sulphonyl chloride (0.250 g, 1 mmol) in pyridine (10 ml). The resulting mixture was stirred at room temperature overnight and then poured into water and extracted with diethyl ether (3×50 ml). The organic extracts were combined, dried and evaporated to leave an oil which was purified by column chromatography (eluant 30% diethyl ether in petroleum ether) to give the title compound as its camphor sulphonate ester (a mixture of diastereoisomers) (0.090 g, 30%, 61% ee).

$^1$H NMR (300 MHz, $CDCl_3$): 4.12(m,2H), 3.59(d,J=15.0 Hz,1H), 2.98(d,J=15.0 Hz,1H), 2.33–2.55(m,2H), 1.15–2.13 (m,8H), 1.11(s,3H), 0.96(d,J=6.9 Hz,3H), 0.91(t,J=7.2 Hz,3H), 0.87(s,3H) ppm.

$^{13}$C NMR (75.5 MHz, $CDCl_3$): 214.7(s), 74.9(t), 58.1(s), 48.1(s), 46.6(t), 42.9(d), 42.7(t), 34.7(d), 27.0(t), 25.6(t), 19.9(q), 19.8(q), 16.2*(q), 16.1*(q), 11.1(q), 11.1(q) ppm. [* Split peaks due to diastereomers.]

EXAMPLE 10
Preparation of (3-ethyl)-1-butene-4-ol.

(Cyclopentadienyl)(1-[(1'S,2'S,5'R)-2'-isopropyl-5'-methylcyclohexyl]-4,5,6,7-tetrahydroindenyl)zirconium dichloride (prepared as in Example 1, 19 mg, 0.04 mmol) was dissolved in a solution of ethylmagnesium bromide (2.6 ml of a 3 M solution in diethyl ether, 8 mmol). 2,5-Dihydrofuran (0.140 g, 2 mmol) was added as a solution in diethyl ether (2 ml). The resulting mixture was stirred at room temperature overnight and then poured into a mixture of ice and aqueous ammonium chloride solution. The aqueous was extracted with diethyl ether (3×50 ml) and the combined organic extracts were evaporated at atmospheric pressure to leave an oil. Camphor sulphonyl chloride (0.500 g, 2 mmol) in pyridine (10 ml) was added to the oil and the resulting mixture was stirred at room temperature overnight. The mixture was then poured into water and extracted with diethyl ether (3×50 ml). The organic extracts were combined, dried and evaporated to leave an oil which was purified by column chromatography (eluant 30% diethyl ether in petroleum ether) to give the title compound as its camphor sulphonate ester (0.138 g, 22%, 92% ee).

$^1$H NMR (300 MHz, $CDCl_3$): 5.59(m,1H), 5.12(m,2H), 4.18(m,3H), 3.57(d,1H), 2.97(d,1H), 0.8–2.5(m,18H), 0.90 (t,3H) ppm.

$^{13}$C NMR (75.5 MHz, $CDCl_3$): 214.6(s), 137.6(d), 117.8 (t), 72.7(t), 58.1(s), 48.1(q), 46.9(t), 45.1(d), 42.9(d), 42.7(t), 27.0(t), 25.0(t), 23.7(t), 19.9(q), 19.8(q), 11.3(q) ppm.

EXAMPLE 11
Preparation of N-(2-hydroxymethylbutyl)-4-benzylpiperidine.

A solution of diethylmagnesium (5 ml of a 0.8 M solution in diethyl ether, 4 mmol) was placed in a Schlenk tube and the solvent removed. The residue was dissolved in THF (1 ml). (Cyclopentadienyl)(1-[(1'S,2'S,5'R)-2'-isopropyl-5'-methylcyclohexyl]-4,5,6,7-tetrahydroindenyl)zirconium dichloride (prepared as in Example 1, 24 mg, 0.05 mmol) was added under positive argon flow followed by N-allyl-4-benzylpiperidine (0.215 g, 1 mmol) in THF (1 ml). The reaction mixture was stirred at room temperature overnight. The mixture was cooled to 0° C. and a balloon of oxygen gas added. The tube was flushed through with a small amount of oxygen and the reaction mixture was stirred overnight. The reaction mixture was poured into aqueous ammonium chloride solution (100 ml) and the aqueous was extracted with diethyl ether (3×50 ml). The organic extracts were combined, dried and evaporated to leave a residue which was purified by column chromatography (eluant 20% diethyl ether in petroleum ether) followed by Kugelrohr distillation (170° C., 1.0 mbar) to give the title compound as a clear oil which crystallised on standing (0.096 g, 37%, 42% ee).

$^1$H NMR (300 MHz, CDCl$_3$): 7.28(tt,J=6.8,1.3 Hz,2H), 7.17(m,3H), 3.77(dt,J=10.5,3.0 Hz,1H), 3.47(t,J=10.3 Hz,1H), 3. 19(d,J=11.4 Hz,1H), 2.84(d,J=11.4 Hz,1H), 2.52 (d,J=7.0 Hz,2H), 2.44(d,J=2.7 Hz,1H), 2.36(t,J=12.5 Hz,1H), 2.06(td,J=11.6,2.2 Hz,2H), 1.87(m,1H), 1,68(m,2H),1.53(m,1H), 1.27(m,2H), 1.08(q,J=6.8 Hz,2H), 0.89(t, J=7.7 Hz,3H) ppm.

$^{13}$C NMR (75.5 MHz, CDCl$_3$): 140.7(s), 129.3(d), 128.4 (d), 126.0(d), 69.8(t), 65.8(t), 56.3(t), 53.0(t), 43.2(t), 38.0 (d), 37.4(d), 32.7(t), 32.1(t), 23.1(t), 12.0(q) ppm.

EXAMPLE 12

Preparation of N-(2-hydroxymethylbutyl)-N-phenylpiperazine.

A solution of diethylmagnesium (5 ml of a 0.8 M solution in diethyl ether, 4 mmol) was placed in a Schlenk tube and the solvent removed. The residue was dissolved in THF (1 ml). (Cyclopentadienyl)(1-[(1'S,2'S,5'R)-2'-isopropyl-5'-methylcyclohexyl]-4,5,6,7-tetrahydroindenyl)zirconium dichloride (prepared as in Example 1, 24 mg, 0.05 mmol) was added under positive argon flow followed by N-allyl-N-phenylpiperazine (0.202 g, 1 mmol) in THF (1 ml). The reaction mixture was stirred at room temperature overnight. The mixture was cooled to 0° C. and a balloon of oxygen gas added. The tube was flushed through with a small amount of oxygen and the reaction mixture was stirred overnight. The reaction mixture was poured into aqueous ammonium chloride solution (100 ml) and the aqueous was extracted with diethyl ether (3×50 ml). The organic extracts were combined, dried and evaporated to leave a residue which was purified by column chromatography (eluant 20% diethyl ether in petroleum ether) followed by Kugelrohr distillation (170° C., 1.0 mbar) to give the title compound as a clear oil which crystallised on standing (0.090 g, 38%, 55% ee).

$^1$H NMR (300 MHz, CDCl$_3$): 7.27(t,J=8.5 Hz,2H), 6.89 (m,3H), 3.79(dt,J=10.5,2.4 Hz,1H), 3.53(t,J=10.3 Hz,1H), 3.20(m,4H), 2.87(m,2H), 2.54(m,4H), 1.94(m,1H), 1.14 (quin,J=6.8 Hz,2H), 0.93(t,J=7.0 Hz,3H) ppm.

$^{13}$C NMR (75.5 MHz, CDCl$_3$): 151.2(s), 129.3(d), 120.1 (d), 116.4(d), 69.7(t), 65.4(t), 53.9(t), 49.4(t), 37.4(d), 23.0 (t), 12.0(q) ppm.

EXAMPLE 13

Preparation of N-(2-methylbutyl)aniline.

(Cyclopentadienyl)(1-[(1'S,2'S,5'R)-2'-isopropyl-5'-methylcyclohexyl]-4,5,6,7-tetrahydroindenyl)zirconium dichloride (prepared as in Example 1, 0.042 g, 0.08 mmol) was dissolved in a solution of diethylmagnesium (7 ml of a 0.832 M solution in diethyl ether, 6 mmol). N-Allylaniline (0.266 g, 2 mmol) was added as a solution in THF (2 ml). The resulting mixture was stirred at room temperature overnight. The mixture was then slowly added (using a syringe) to concentrated hydrochloric acid at 0° C. The aqueous phase was extracted with diethyl ether. The ethereal extracts were combined, dried and evaporated to leave (cyclopentadienyl)(1-[(1'S,2'S,5'R)-2'-isopropyl-5'-methylcyclohexyl]-4,5,6,7-tetrahydroindenyl)zirconium dichloride (46 mg of 90% pure material).

The aqueous phase was then neutralised with sodium hydroxide solution (2M) and extracted again with diethyl ether (3×50 ml). The organic extracts were combined, dried and evaporated to leave an oil which was Kugelrohr distilled (155° C., >O. lmbar) to furnish the title compound as a clear oil (0.180 g, 55%).

EXAMPLE 14

Preparation of 2-ethyl-trans-4-phenyl-3-butene-1-ol, 2-ethyl-1-phenyl-3-butene-1-ol, 2-ethyl-trans-4-(4-fluorophenyl)-3-butene-1-ol and 2-ethyl-1-(4-fluorophenyl)-3-butene-1-ol. (Cyclopentadienyl)(1-[(1'S, 2'S,5'R)-2'-isopropyl-5'-methylcyclohexyl]-4,5,6,7-tetrahydroindenyl)zirconium dichloride (prepared as in Example 1, 48 mg, 0.1 mmol, 5 mol %) was dissolved in ethylmagnesium chloride solution (5 ml of a 2 M solution in diethyl ether, 10 mmol) at room temperature, 2-phenyl-2,5-dihydrofuiran (0.292 g, 2 mmol) in diethyl ether (2 ml) was added, and the reaction stirred at room temperature for 34 hours. The mixture was cooled and poured into ammonium chloride solution (50 ml). The products were extracted into diethyl ether, seperated by column chromatography (eluant 20% diethyl ether in petroleum ether) and Kugelrohr distilled to afford 2-ethyl-trans-4-phenyl-3-butene-1-ol (52% yield, 78% ee) and 2-ethyl-1-phenyl-3-butene-1-ol (42% yield, 82% ee). In a similar fashion, except that the reaction time was 10 hours at 40° C., 2-(4-fluorophenyl)-2,5-dihydrofuran gave 2-ethyl-trans-1-(4-fluorophenyl)-3-butene-1-ol (53% yield, 75% ee) and 2-ethyl-1-(4-fluorophenyl)-3-butene-1-ol (27% yield, 74% ee).

2-Ethyl-trans-4-(4-fluorophenyl)-3-butene-1-ol: $^1$H NMR (300 MHz; CDCl$_3$): δ 7.34(dd,J=8.8, 5.1 Hz, 2H), 7.00(t,J= 8.0 Hz,2H), 6.46(d,J=15.5 Hz, 1H), 5.91(dd,J=16.2, 8.8 Hz, 1H), 3.66(dd,J=11.1, 5.1 Hz, 1H), 3.52(dd, J=10.3, 8.0 Hz, 1H), 2.30(m, 1H), 1.54(m,2H), 1.36(m,1H), 0.95(t,J=7.4 Hz, 3H)ppm.

$^{13}$C NMR (75.5 MHz; CDCl$_3$): δ 162.3, 133.5, 131.5, 131.3, 127.7, 115.5, 66.0, 48.2, 24.2, 11.9 ppm.

2-Ethyl-1-(4-fluorophenyl)-3-butene-1-ol: $^1$H NMR (300 MHz; CDCl$_3$): δ 7.30(m,2H), 7.03(t,J=8.7 Hz, 2H), 5.64 (ddd, J=16.9, 9.6, 9.6 Hz, 1H), 5.30(dd,J=10.3, 1.5 Hz, 1H), 5.22(dd,J=16.9, 2.2 Hz, 1H), 4.39(d,J=7.4 Hz, 1H), 2.24(brs, 1H), 2.15(m,1H), 1.19(m,2H), 0.79(t,J=7.4 Hz, 3H)ppm.

$^{13}$C NMR (75.5 MHz; CDCl$_3$): δ 162.4, 139.05, 138.4, 128.6, 119.5, 115.2, 76.0, 55.0, 23.5, 11.9 ppm.

EXAMPLE 15

Preparation of 1-(1-pyrrolidinyl)-1-phenylethane.

(Cyclopentadienyl)(1-[(1'S,2'S,5'R)-2'-isopropyl-5'-methylcyclohexyl]4,5,6,7-tetrahydroindenyl) titanium dichloride (22 mg, 0.05 mmol, 1 equivalent, as prepared in Example 4) was dissolved in tetrahydrofuran (5 ml) and Red-Al (0.11 ml of 33% weight solution in toluene, 0.2 mmol, 2 equivalents) added turning the red solution dark grey/purple. Phenylsilane (30 μL) was then added. This mixture was stirred at room temperature for an hour before a solution of 1-phenyl-1-(1-pyrrolidinyl)-ethene (0.173 g, 1 mmol, 20 equivalents) in tetrahydrofuran (2 ml) was added via a syringe turning the reaction brown. The reaction flask was then evacuated and refilled with hydrogen gas before being stirred overnight. The reaction was poured into water and the title compound was extracted into dilute hydrochloric acid (2M). The acid washings were then made strongly basic with sodium hydroxide and the product was extracted into diethylether. The solvent was removed to yield a yellow oil (60 mg, 34%) shown to be a 30% enantiomeric excess by NMR in the presence of (R)-O-acetylmandelic acid. (See N. E. Lee and S. L. Buchwald, *J. Am. Chem. Soc.* 1994, 116, 5985–6.)

When this reaction was repeated at 500 p.s.i. of hydrogen the product was isolated in 66% yield and 49% enantiomeric excess.

EXAMPLE 16

Preparation of phenyl(2-methylbutyl)sulphide.

Hexane (1 ml) was added to (cyclopentadienyl)(1-[(1'S, 2'S,5'R)-2'-isopropyl-5'-methylcyclohexyl]-4,5,6,7-tetrahydroindenyl)zirconium dichloride complex (20 mg, 4 mol %, prepared as in Example 1) in a 25 ml schlenk flask containing a stirring bar. Allylphenylthioether (150 mg, 1 mmol) was added and the flask evacuated and refilled 3 times with argon. Triethylaluminum (6 ml, 1.0 M in hexane, 6 mmol, 6 eq) was added dropwise. The solution turned yellow and was left for 72 hours. Water (10 ml) was added dropwise, the organics were extracted with diethylether (3×5 ml) and the combined extracts were dried over magnesium sulphate. The solvents were removed under reduced pressure and Kugelrohr distillation yielded the title compound as a clear liquid (145 mg, 0.85 mmnol, 80.5% yield, e.e 57% (FS-Hydrodex-B, 110° C.)).

EXAMPLE 17
Hydrogenation of 2-phenyl-1-butene.
(1R,7S)-1,3,10,10-Tetramethyltricyclo-[5.2.1 .0$^{2,6}$]-deca-2,5-dienyl)($\eta^5$-cyclopentadienyl)titanium dichloride (21 mg, 0.05 mmol, prepared as in Example 6) together with 2-phenyl-1-butene (132 mg, 1 mmol) and freshly distilled toluene (5 ml) were placed into a 50 ml round-bottomed flask. After degassing with three freeze/thaw cycles the vessel was filled with hydrogen (3 evacuate/refill cycles). n-Butyllithium (0.2 ml, 22.5 M, 0.5 mmol) was then added via syringe at room temperature and the resulting dark grey/green reaction mixture was stirred under a pressure of 20 p.s.i. hydrogen, while excluding light, for 40 hours. The hydrogen pressure was vented and the reaction vessel opened to air. Aqueous hydrochloric acid (2 ml, 5 M) was added and mixture was stirred for 5 minutes. The organic phase was separated and the aqueous phase extracted with ether (3×5 ml). The combined organic phases were dried (sodium sulphate) and the solvents removed iii vacuo to provide 2-phenylbutane (56 mg, 0.42 mmol) of 10.3% ee (assessed using gas chromatography, Astec α-DA column, 65° C.).

EXAMPLE 18
Ethylalumination of 1-hexene.
To a solution of (cyclopentadienyl)(1-[(1'S,2'S,5'R)-2'-isopropyl-5'-methylcyclo-hexyl]-4,5,6,7-tetrahydroindenyl) zirconium dichloride (39.7 mg. 0.08 mmol, 8 mol %, prepared as in Example 1) in dichloromethane (3 ml) was added triethylaluminium (1 ml of a 1.0 M solution in hexanes, 1 mmol) dropwise over 5 minutes at room temperature. To this solution was added 1-hexene (0.125 ml, 1 mmol) and the solution stirred at room temperature for 12 hours. Oxygen was then bubbled through the mixture for 30 minutes, after which the reaction mixture was stirred under an atmosphere of oxygen for 6 hours. Aqueous sodium hydroxide solution (10 ml, 15% solution) was then added and the products extracted into ether (3×5 ml). Removal of solvent and chromatography gave pure 2-ethyl-1-hexanol (62.6 mg, 48%) with a 25% ee (gas chromatography analysis (FS-Hydrodex-β-3P)).

EXAMPLE 19
Preparation of N-(2-methylthiomethyletherbutyl)aniline.
To a flask which had ben flame dried under vacuum, containing ($\eta^5$-(1R,7S)-1,3,10,10-tetramethyltricyclo [5.2.1.0$^{2,6}$]-deca-2,5-dien-4-yl)($\eta^5$-cyclopentadienyl) zirconium dichloride (prepared as in Example 5, 15 mg, 0.04 mmol, 4 mol %) and allylaniline (0.125 g, 1.05 mmol) was added THF (1 ml) followed by ethylmagnesium chloride (2.6 ml of a 2.0 M solution in THF, 5.25 mmol). The reaction was stirred at room temperature in the dark for 60 hours before addition of dimethylsulphide (1 ml) and work-up as in Example 8, to give the title compound (60 mg, 35% yield, 29.6% ee).

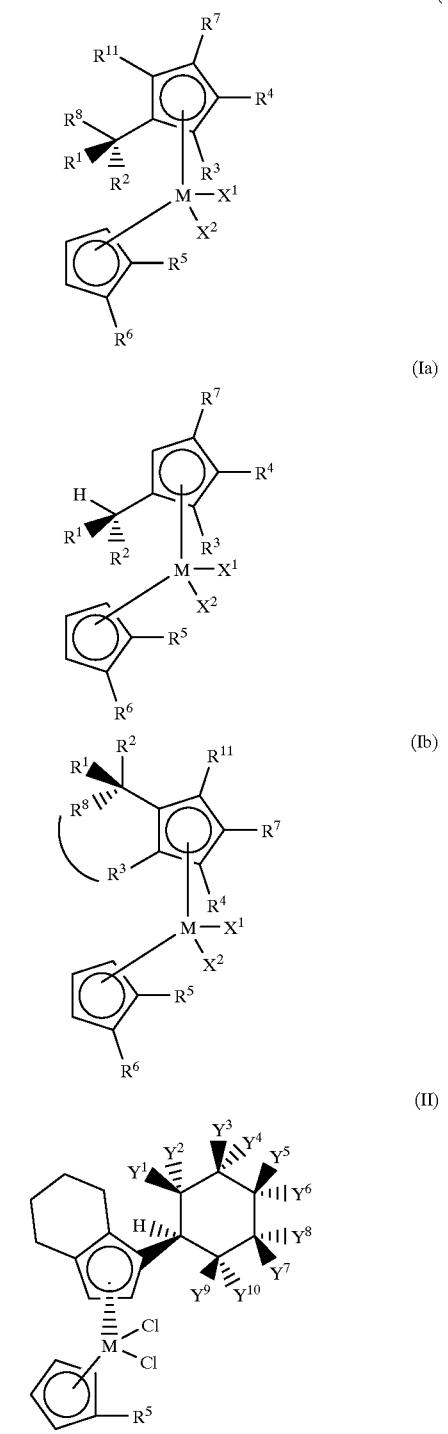

(II')
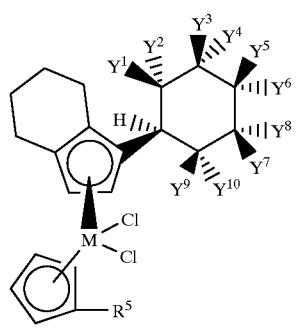
(IIa)
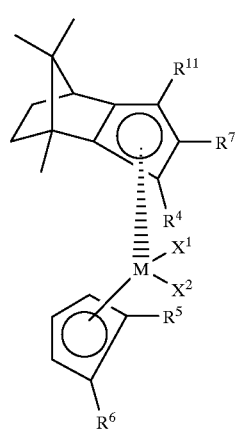
(IIb)
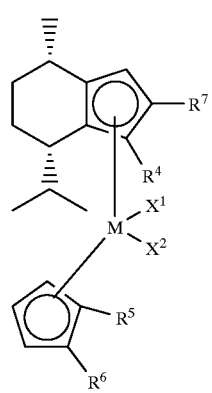
(IIc)
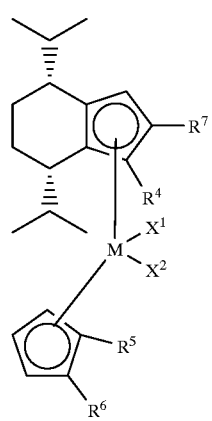
(IId)
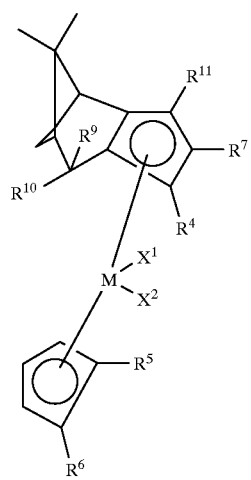
(IIe)
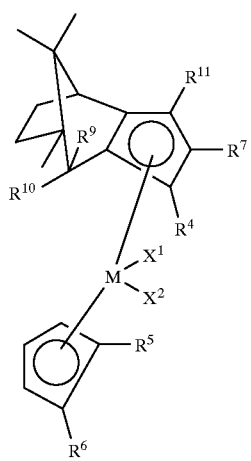
(IIf)
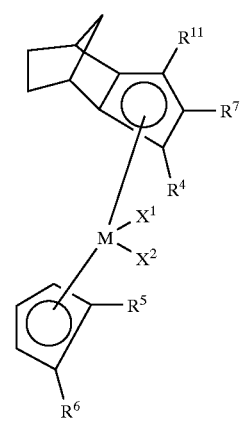

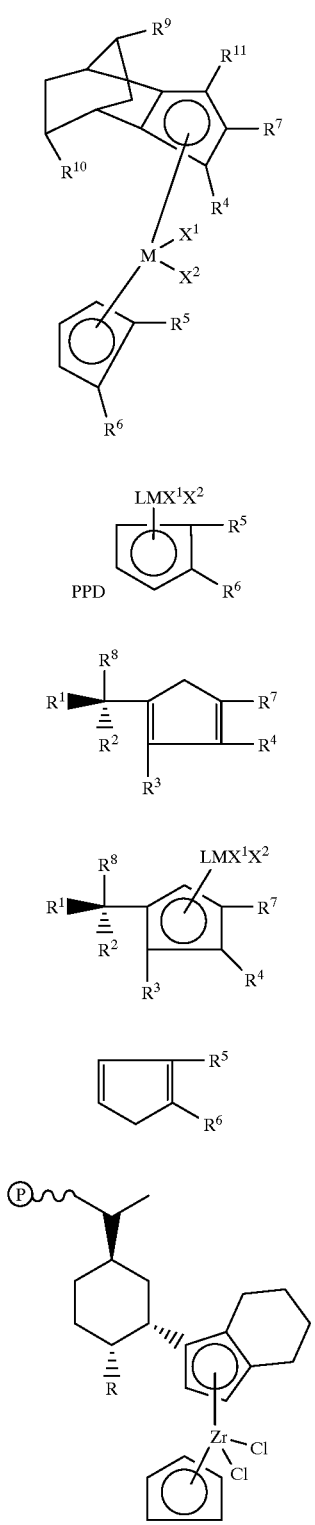

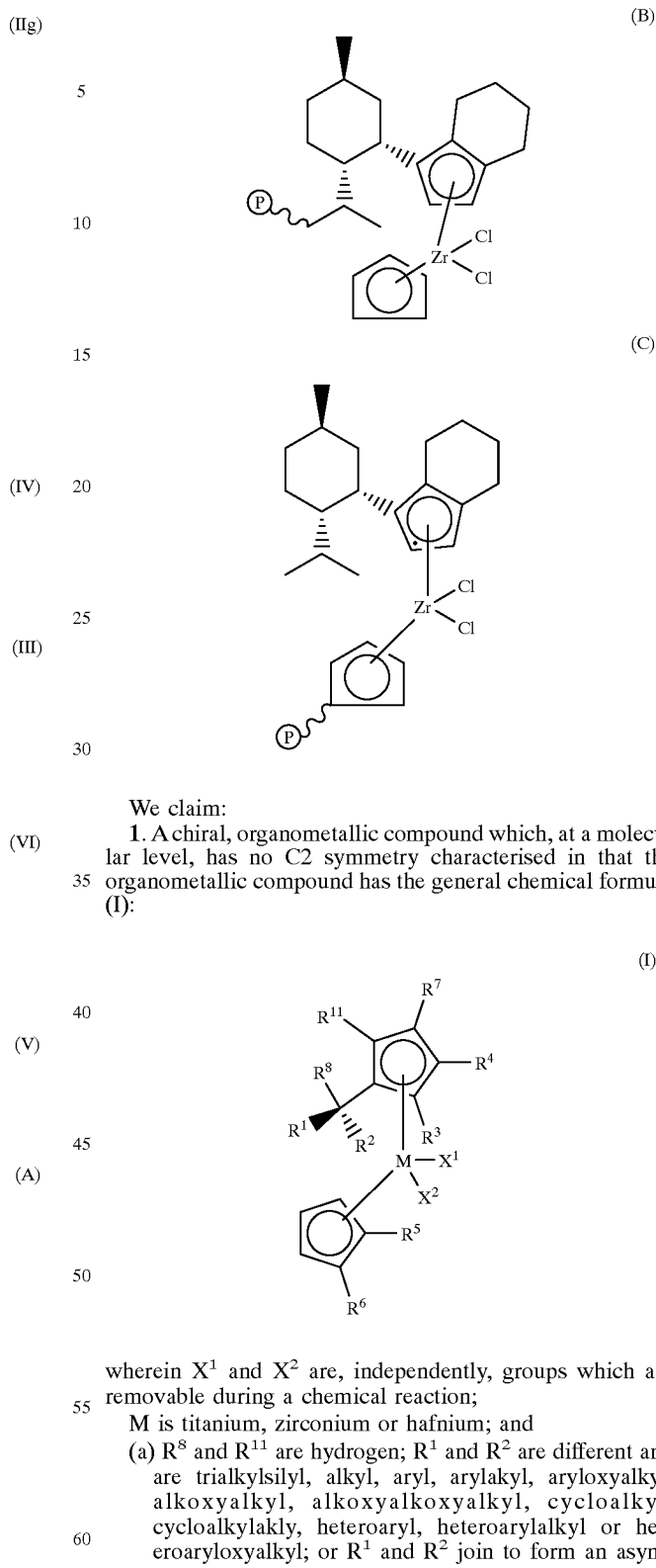

We claim:

1. A chiral, organometallic compound which, at a molecular level, has no C2 symmetry characterised in that the organometallic compound has the general chemical formula (I):

wherein $X^1$ and $X^2$ are, independently, groups which are removable during a chemical reaction;

M is titanium, zirconium or hafnium; and (a) $R^8$ and $R^{11}$ are hydrogen; $R^1$ and $R^2$ are different and are trialkylsilyl, alkyl, aryl, arylakyl, aryloxyalkyl, alkoxyalkyl, alkoxyalkoxyalkyl, cycloalkyl, cycloalkylakly, heteroaryl, heteroarylalkyl or heteroaryloxyalkyl; or $R^1$ and $R^2$ join to form an asymmetrically substituted $C_{3-8}$ cycloalkyl, $C_{3-8}$ cycloalkenyl or $C_{3-8}$ heterocyclyl ring optionally substituted with hydroxy, trialkylsilyl, alkyl, alkoxy, aryl, arylalkyl, aryloxyalkyl, alkoxyalkoxyalkyl, cycloalkyl, cycloalkylalky, heteroaryl, heteroarylalkyl or heteroaryloxyalkyl; $R^3$ is as defined for $R^1$; $R^4$, $R^5$, $R^6$ and $R^7$ are the same or different and are hydrogen or as defined above for $R^1$; or one or more of $R^3$ and $R^4$, $R^4$ and $R^7$ or $R^5$ and $R^6$ join to formn an optionally substituted saturated or unsaturated ring optionally comprising one or more heteroatoms; or $R^3$, $R^4$ or $R^7$ joins with $R^5$ to form an optionally substituted $C_{1-3}$ alkyl or optionally substituted silyl bridge; or (b) $R^3$ and $R^8$ join to form an optionally substituted non-aromatic ring system optionally comprising one or more heteroatoms and $R^1$ and $R^2$ are different and are hydrogen, trialkylsilyl, alkyl, aryl, arylalkyl, aryloxyalkyl, alkoxyalkyl, alkoxyaryloxyalkyl, cycloalkyl, cycloalkylalkyl, heteroaryl, heteroarylalkyl or heteroaryloxyalkyl; or $R^1$, $R^3$ and $R^8$ join to form an optionally substituted non-aromatic ring system optionally comprising one or more heteroatoms and $R^2$ is hydrogen, trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; one of $R^4$ and $R^{11}$ is hydrogen, the other being trialkylsilyl, alkyl, aryl, arylalkyl, aryloxyalkyl, alkoxyalkyl, alkoxyaryloxyalkyl, cycloalkyl, cycloalkylalkyl, heteroaryl, heteroarylalkyl or heteroaryloxyalkyl; $R^5$, $R^6$ and $R^7$ may be the same or different and are selected from the substitiuents already recited for $R^2$; or, one or more of $R^5$ and $R^6$ or $R^7$ and whichever of $R^4$ and $R^{11}$ is not hydrogen to join to form an optionally substituted saturated or unsaturated ring optionally comprising one or more heteroatams; or $R^5$ joins with one of $R^6$, $R^7$ or whichever of $R^4$ and $R^{11}$ is not hydrogen to form an optionally substituted $C_{1-3}$ alkyl bridge or optionally substituted silyl bridge.

2. A compound as claimed in claim 1 having the formula (Ia):

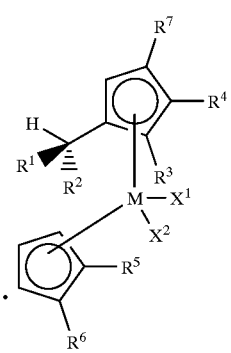

(Ia)

wherein $R^1$ and $R^2$ are different and are trialkylsilyl, alkyl, aryl, arylalkyl, aryloxyalkyl, alkoxyalkyl, alkoxyalkoxyalkyl, cycloalkyl, cycloalkylalky, heteroaryl, heteroarylalkyl or heteroaryloxyalkyl; or $R^1$ and $R^2$ join to form an asymmetrically substituted $C_{3-8}$ cycloalkyl, $C_{3-8}$ cycloalkenyl or $C_{3-8}$ heterocyclyl ring optionally substituted with hydroxy, trialkylsilyl, alkyl, alkoxy, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^3$ is as defined for $R^1$; $R^4$, $R^5$, $R^6$ and $R^7$ are the same or different and are hydrogen or as defined above for $R^1$; or one or more of $R^3$ and $R^4$, $R^4$ and $R^7$ or $R^5$ and $R^6$ join to form an optionally substituted saturated or unsaturated ring optionally comprising one or more heteroatoms; or $R^3$, $R^4$ or $R^7$ joins with $R^5$ to form an optionally substituted $C_{1-3}$ alkyl or optionally silyl bridge; $X^1$ and $X^2$ are, independently, groups which are removable during a chemical reaction; and M is titanium, zirconium or hafnium.

3. A compound as claimed in claim 1 having the formula (Ia):

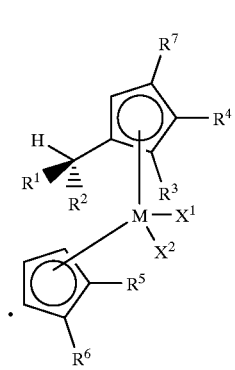

(Ia)

wherein $R^1$ and $R^2$ are different and are trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$ and $R^2$ join to form an asymmetrically substituted $C_{3-8}$ cycloalkyl, $C_{3-8}$ cycloalkenyl or $C_{3-8}$ heterocyclyl ring optionally substituted with hydroxy, trialkylsilyl, alkyl, alkoxy, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^3$ as defined for $R^1$; $R^4$, $R^5$ and $R^6$ are the same or different and are hydrogen or as defined for $R^1$ above; or $R^3$ and $R^4$ or $R^5$ and $R^6$ or both join to form an optionally substituted saturated or unsaturated ring comprising one or more heteroatoms; $R^7$ is hydrogen or alkyl; or $R^3$, $R^4$ or $R^7$ joins with $R^5$ to form an optionally substituted $C_{1-3}$ alkyl or optionally silyl bridge; $X^1$ and $X^2$ are, independently, groups which are removable during a chemical reaction; and M is titanium, zirconium or hafnium.

4. A compound as claimed in claim 1 having the formula (Ib):

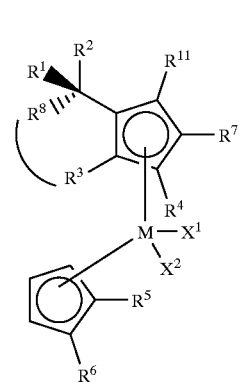

(Ib)

wherein
$X^1$ and $X^2$ are, independently, groups which are removable during a chemical reaction;
M is titanium, zirconium or hafnium;
$R^3$ and $R^8$ join to form an optionally substituted non-aromatic ring system optionally comprising one or more heteroatoms and $R^1$ and $R^2$ are different and are hydrogen, trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; or $R^1$, $R^3$ and $R^8$ join to form an optionally substituted non-aromatic ring system optionally comprising one or more heteroatoms and $R^2$ is hydrogen, trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; one of $R^4$ and $R^{11}$ is hydrogen, the other being trialkylsilyl, alkyl, aryl, arylalkyl, aryloxyalkyl, alkoxyalkyl, alkoxyalkoxyalkyl, cycloalkyl, cycloalkylalkyl, heteroaryl, heteroarylalkyl or heteroaryloxyalkyl; $R^5$, $R^6$ and $R^7$ may be the same or different and are selected from the substituents already recited for $R^2$; or, one or more of $R^5$ and $R^6$ or $R^7$ and whichever of $R^4$ and $R^{11}$ is not hydrogen join to form an optionally substituted saturated or unsaturated ring optionally comprising one or more heteroatoms, or $R^5$ joins with one of $R^3$, $R^7$ or whichever of $R^4$ and $R^{11}$ is not hydrogen to form an optionally substituted $C_{1-3}$ alkyl bridge or optionally substituted silyl bridge.

5. A compound as claimed in claim 1, 2, or 3 wherein $R^3$ and $R^4$ or $R^5$ and $R^6$ or both join to form an optionally substituted unsaturated or saturated ring comprising one or more heteroatoms.

6. A compound as claimed in claim 1, 2, 3 or 5 wherein $R^3$ and $R^4$ join together to form (in conjunction with the cyclopentadiene ring to which they are attached) a 6 membered non-aromatic carbocyclic ring.

7. A compound as claimed in claim 1, 2, 3 or 5 wherein $R^3$ is $C_{1-4}$ alkyl; $R^4$ is hydrogen or $C_{1-4}$ alkyl; or $R^3$ and $R^4$ join together to form (in conjunction with the cyclopentadiene ring to which they are attached) a 5, 6 or 7 membered non-aromatic carbocyclic ring; and $R^7$ is hydrogen or $C_{1-4}$ alkyl.

8. A compound as claimed in claim 1, 2, or 3 wherein $R^1$ is $C_{1-4}$ alkyl, phenyl, tri($C_{1-4}$ alkyl)silyl or phenyl($C_{1-4}$) alkyl; and $R^2$ is $C_{1-4}$ alkyl; or $R^1$ and $R^2$ join to form an asymmetrically substituted $C_{3-8}$ cycloalkyl ring optionally substituted with alkyl or phenylalkyl.

9. A compound as claimed in any one of claims 1 to 4 wherein $R^7$ is hydrogen.

10. A compound as claimed in claim 1 or 4 wherein when $R^{11}$ is hydrogen $R^4$ and $R^7$ join together to form (in conjunction with the cyclopentadiene ring to which they are attached) a 6 membered non-aromatic carbocyclic ring; or when $R^4$ is hydrogen $R^{11}$ and $R^7$ join together to form (in conjunction with the cyclopentadiene ring to which they are attached) a 6 membered non-aromatic carbocyclic ring.

11. A compound as claimed in any one of claims 4 to 10 wherein $R^5$ and $R^6$ join to form an optionally substituted unsaturated or saturated ring optionally comprising one or more heteroatoms.

12. A compound as claimed in any one of claims 1 to 4 wherein $R^5$ and $R^6$ are both hydrogen.

13. A compound as claimed in any one of claims 1 to 4 wherein $X^1$ and $X^2$ are, independently, halogen, alkyl, alkoxy, alkenyl, alkynyl, cycloalkyl, aryl or aryloxy.

14. A compound as claimed in claim 13 wherein $X^1$ and $X^2$ are, independently, halogen.

15. A compound as claimed in any one of claims 1 to 4 wherein M is zirconium.

16. A compound as claimed in claim 2 or 3 wherein $R^1$ and $R^2$ join to form an asymmetrically substituted $C_{3-8}$ cycloalkyl ring optionally substituted with alkyl or phenylalkyl; $R^3$ and $R^4$ join together to form (in conjunction with the cyclopentadiene ring to which they are attached) a 6 membered non-aromatic carbocyclic ring; $R^5$, $R^6$ and $R^7$ are all hydrogen; and $X^1$ and $X^2$ are, independently, chlorine or bromine.

17. A compound of formula (II) or (II'):

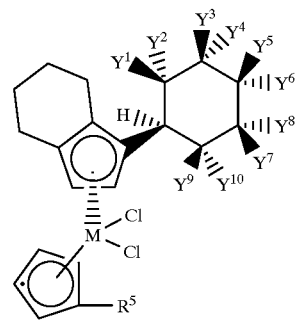

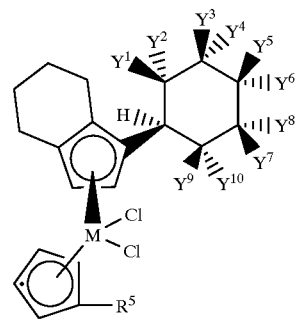

or an enantiomer thereof, wherein $R^5$ is hydrogen or $C_{1-4}$ alkyl; M is zirconium, titanium or hafnium; $Y^1$ is $C_{1-6}$ alkyl, tri($C_{1-4}$)alkylsilyl or phenyl($C_{1-4}$)alkyl; $Y^2$, $Y^3$, $Y^4$, $Y^5$, $Y^6$ and $Y^7$ are all hydrogen; $Y^8$ and $Y^9$ are, independently, hydrogen or $C_{1-4}$ alkyl; and $Y^{10}$ is hydrogen, $C_{1-4}$ alkyl or tri($C_{1-4}$)alkylsilyl.

18. A compound as claimed in any one of claims 17 or 1 to 4 which is bound to a polymer support.

19. A process for preparing a compound as claimed in claim 1, the process comprising either:

(a) deprotonating a compound of formula (III)

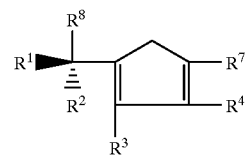

and reacting the product obtained with a compound of formula (IV)

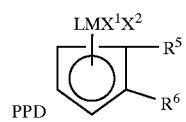

wherein R1 to R8, M, $X^1$, X2 are as defined in claim 22 and L is a suitable leaving group;

(b) deprotonating a compound of formula (V)

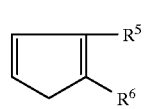
(V)

and reacting the product obtained with a compound of formula (VI)

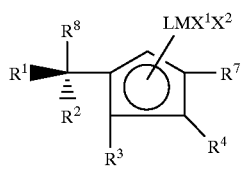
(VI)

wherein $R^1$ to $R^8$, L, M, $X^1$ and $X^2$ are as defined above;

(c) reacting a trialkylsilyl or trialkylstannyl derivative of a compound of formula (III)

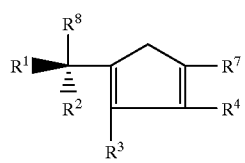
(III)

with a compound of formula (IV)

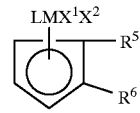
(IV)

wherein $R^1$ to $R^8$, L, M, $X^1$ and $X^2$ are as defined above;

(d) reacting a trialkylsilyl or trialkylstannyl derivative of a compound of formula (V)

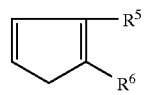
(V)

with a compound of formula (VI)

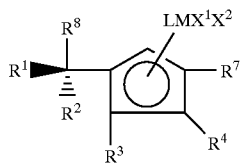
(VI)

wherein $R^1$ to $R^8$, M, L, $X^1$ and $X^2$ are as defined above;

e) when $R^3$ and $R^4$ join to form a saturated, non-aromatic, carbocyclic ring, hydrogenating a compound of formula (I)

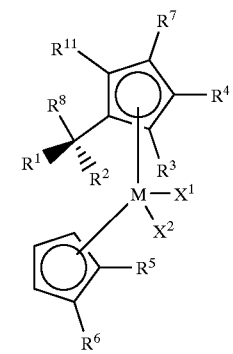
(I)

wherein $R^3$ and $R^4$ join to form an aromatic ring, under suitable conditions, wherein $R^1$, $R^2$, $R^5$, $R^6$, $R^7$, $R^8$, M, $X^1$ and $X^2$ are as defined above; or (f) when $R^3$ and $R^4$ form a saturated ring and M is titanium, chemically modifying the nature the ligand incorporating $R^3$ and $R^4$ whilst the ligand is attached to zirconium, removing the ligand from zirconium with a suitable base and attaching the ligand to a compound of formula (IV)

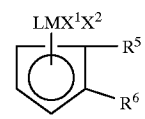
(IV)

wherein $R^1$, $R^2$, $R^5$, $R^6$, $R^7$, $R^8$, L, M, $X^1$ and $X^2$ are as defined above.

* * * * *